United States Patent [19]
Shioiri et al.

[11] Patent Number: 6,071,943
[45] Date of Patent: Jun. 6, 2000

[54] IMIDAZOLE DERIVATIVE AND MEDICINE COMPRISING THE SAME AS ACTIVE INGREDIENT

[75] Inventors: Noriaki Shioiri, Narita; Tadashi Mikami, Sawara; Shinichi Morimoto, Sakura; Kazuo Yamazaki, Sawara; Hiroyuki Naito, Narita; Junji Okawa, Chiba; Noriyuki Kawamoto, Narita; Hiroshi Hasegawa, Sakura; Koichi Tachibana; Susumu Sato, both of Narita; Toshio Yokoyama, Tokyo, all of Japan

[73] Assignee: SSP Co. Ltd., Tokyo, Japan

[21] Appl. No.: 09/200,750

[22] Filed: Nov. 30, 1998

[30] Foreign Application Priority Data

Dec. 16, 1997 [JP] Japan ................................. 9-346215

[51] Int. Cl.$^7$ ................. A01N 43/50; C07D 233/64; C07D 233/70
[52] U.S. Cl. .................. 514/400; 548/341.5; 548/336.1
[58] Field of Search ........................ 548/341.5; 514/400

[56] References Cited

FOREIGN PATENT DOCUMENTS

| 0 284 914 | 10/1988 | European Pat. Off. . |
| 1 935 685 | 1/1971 | Germany . |
| 7-36069 | 2/1995 | Japan . |

OTHER PUBLICATIONS

Oganesyan et al., Electronic structure activity relationships for propenone derivatives, Khim.—Farm. Zh., 29(10), pp. 28–30, Dec. 1995.

D.G. Batt, et al., Journal of Medicinal Chemistry, vol. 36, No. 10, pps. 1434–1442, "2'–Substituted Chalcone Derivatives as Inhibitors of Interleukin–1 Biosynthesis", 1993.

*Primary Examiner*—Joseph McKane
*Assistant Examiner*—Dominic Keating
*Attorney, Agent, or Firm*—Oblon, Spivak, McClelland, Maier & Neustadt, P.C.

[57] ABSTRACT

Disclosed herein are an imidazole derivative represented by the following general formula (1):

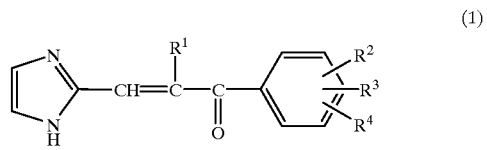

(1)

wherein $R^1$ is a hydrogen atom, or an alkyl, alkoxy or alkoxycarbonyl group, and $R^2$, $R^3$ and $R^4$ are the same or different from one another and are independently a hydrogen or halogen atom, an alkyl, halogenoalkyl, hydroxyl or alkoxy group, or the like, or a salt thereof, and a medicine comprising such a compound. The compound specifically suppresses the production of particular cytokine and is hence useful as an active ingredient for immune function modulators and the like.

7 Claims, No Drawings

IMIDAZOLE DERIVATIVE AND MEDICINE COMPRISING THE SAME AS ACTIVE INGREDIENT

BACKGROUND OF THE INVENTION

1. Field of the Invention

The present invention relates to imidazole derivatives, and particularly to novel imidazole derivatives and salts thereof, which combine an excellent suppressive effect on the production of cytokine with high safety and are useful as medicines such as immune function modulators.

2. Description of the Background Art

An immune system inherent in the viable body, which is a protective mechanism against extrinsic or intrinsic foreign bodies, consists of a cell group of the monocytic series, typified by a macrophage and a neutrophil, and a cell group of the lymphocytic series composed of a T cell and a B cell. These cell groups not only separately function, but also maintain the homeostasis by direct contact between the cells or interaction through a soluble factor generally designated cytokine. The mechanism thereof is minute in the extreme, and a subtle breakdown of the balance induces a serious morbid state.

For example, a collagen disease, systemic lapus erythematosus, and various allergic diseases are said to be caused as a result that the regulatory mechanism of such immunocytes is broken down, whereby autoantibodies are produced, and an excess immune reaction is induced. In AIDS (acquired immunodeficiency syndrome), it is also known that the immune mechanism is broken down by infecting a T cell with HIV, and its morbid state is allowed to progress. It has also been definitely shown that the breakdown of the balance in the immune system forms a cause that the morbid states of diabetes, viral chronic diseases and cancer are allowed to progress.

In recent years, cytokine-production suppressors such as cyclosporin and FK506 already known as rejection suppressors upon organ transplantation have been used for diseases caused as a result of an excess immune reaction. Besides, anti-inflammatory steroid agents having a cytokine-production suppressing effect have also been used for autoimmune diseases such as allergy, atopy and rheumatism, and bronchial asthma, and some therapeutic effect has been achieved.

However, these immunosuppressive agents and anti-inflammatory steroid agents are such that the production of many kinds of cytokine is suppressed. Therefore, the administration of such an agent to a patient suffering from an autoimmune disease in particular has required to take measures such as the limitation of an administration method and the administration of the agent with an intermission from the viewpoint of safety.

SUMMARY OF THE INVENTION

It is accordingly an object of the present invention to provide an immune function modulator which strongly suppresses only the production of particular cytokine and has high safety.

In view of the foregoing circumstances, the present inventors have synthesized a large number of compounds to carry out an extensive investigation as to their suppressive effects on the production of cytokine. As a result, it has been found that imidazole derivatives represented by a general formula (1), which will be described subsequently, or salts thereof strongly suppress the production of interleukin 4 (IL-4) which is produced mainly by a T helper cell type 2 (Th2), takes part in the differentiation of a B cell and deeply joins in an allergic reaction through IgE, and are useful as immune function modulator, thus leading to completion of the present invention. It has also been found that most of the compounds represented by the general formula (1) are novel.

According to the present invention, there is thus provided a medicine comprising, as an active ingredient, an imidazole derivative represented by the following general formula (1):

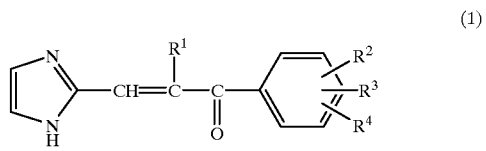

(1)

wherein $R^1$ is a hydrogen atom, or an alkyl, alkoxy or alkoxycarbonyl group, and $R^2$, $R^3$ and $R^4$ are the same or different from one another and are independently a hydrogen or halogen atom, or an alkyl group, a halogenoalkyl group, a hydroxyl group, an alkoxy group, a carboxyl group, a nitro group, a tetrahydropyranyloxy group, an alkoxyalkoxy group, an alkoxycarbonyl group, a cyano group, a tetrazolyl group, a phenyl group which may be substituted, a phenoxy group which may be substituted, a benzyloxy group which may be substituted, an amino group which may be substituted, or a dioxolanyl group which may be substituted, or $R^3$ and $R^4$ may form a fused aromatic ring, which may be substituted, together with a benzene ring on which $R^3$ and $R^4$ are substituted, or a salt thereof.

According to the present invention, there is also provided a medicinal composition comprising the imidazole derivative represented by the general formula (1) or the salt thereof and a pharmaceutically acceptable carrier.

According to the present invention, there is further provided use of the imidazole derivative represented by the general formula (1) or the salt thereof for a medicine.

According to the present invention, there is still further provided a method of treating a disease based on the production of cytokine, or a disease caused by immune function disorder, which comprises administering an effective amount of the imidazole derivative represented by the general formula (1) or the salt thereof.

According to the present invention, there is yet still further provided an imidazole derivative represented by the following general formula (1'):

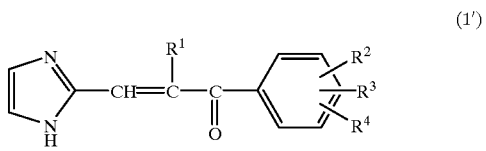

(1')

wherein $R^1$ is a hydrogen atom, or an alkyl, alkoxy or alkoxycarbonyl group, and $R^2$, $R^3$ and $R^4$ are the same or different from one another and are independently a hydrogen or halogen atom, or an alkyl group, a halogenoalkyl group, a hydroxyl group, an alkoxy group, a carboxyl group, a nitro group, a tetrahydropyranyloxy group, an alkoxyalkoxy group, an alkoxycarbonyl group, a cyano group, a tetrazolyl group, a phenyl group which may be substituted, a phenoxy group which may be substituted, a benzyloxy group which may be substituted, an amino group which may be substituted, or a dioxolanyl group which may be substituted, or $R^3$ and $R^4$ may form a fused aromatic ring, which may be substituted, together with a benzene ring on which $R^3$ and $R^4$ are substituted, with the proviso that $R^1$, $R^2$, $R^3$ and $R^4$ are not hydrogen atoms at the same time, or a salt thereof.

The imidazole derivatives (1) or the salts thereof according to the present invention specifically suppress the production of cytokine, particularly, IL-4, and are hence useful as active ingredients for cytokine-production suppressors or immune function modulators, more specifically, for rejection suppressors upon organ transplantation, and agents for preventing and treating diseases based on the production of cytokine, such as autoimmune diseases such as allergy, atopy and rheumatism, bronchial asthma, IgA nephropathy, osteoporosis, inflammation, cancer, and HIV infection, particularly, diseases caused by immune function disorder.

The above and other objects, features and advantages of the present invention will be readily appreciated as the same becomes better understood from the preferred embodiments of the present invention, which will be described subsequently in detail, and from the appended claims.

DETAILED DESCRIPTION OF THE PREFERRED EMBODIMENTS

In the general formula (1) which represents the imidazole derivatives according to the present invention, the alkyl group represented by $R^1$ includes linear, branched and cyclic alkyl groups. The linear or branched group is preferably an alkyl group having 1 to 8 carbon atoms, and examples thereof include methyl, ethyl, n-propyl, isopropyl, n-butyl, isobutyl, n-pentyl, n-hexyl, n-heptyl and n-octyl groups. The cyclic alkyl group is preferably that having 3 to 8 carbon atoms, and examples thereof include cyclopropyl, cyclobutyl, cyclopentyl, cyclohexyl, cycloheptyl and cyclooctyl groups. The alkoxy group is preferably that having 1 to 6 carbon atoms, and examples thereof include methoxy, ethoxy, n-propoxy, isopropoxy, n-butoxy, isobutoxy, t-butoxy, n-pentyloxy and n-hexyloxy groups. The alkoxy group of the alkoxycarbonyl group is preferably an alkoxy group having 1 to 6 carbon atoms, and examples thereof include methoxy, ethoxy, n-propoxy, isopropoxy, n-butoxy, isobutoxy, t-butoxy, n-pentyloxy and n-hexyloxy groups.

In the general formula (1), examples of the halogen atom represented by $R^2$, $R^3$ or $R^4$ include fluorine, chlorine, bromine and iodine atoms. The alkyl group includes linear, branched and cyclic alkyl groups. The linear or branched group is preferably an alkyl group having 1 to 8 carbon atoms, and examples thereof include methyl, ethyl, n-propyl, isopropyl, n-butyl, isobutyl, sec-butyl, t-butyl, n-pentyl, n-hexyl, n-heptyl and n-octyl groups. The cyclic alkyl group is preferably that having 3 to 8 carbon atoms, and examples thereof include cyclopropyl, cyclobutyl, cyclopentyl, cyclohexyl, cycloheptyl and cyclooctyl groups. Examples of the halogenoalkyl group include those with at least one halogen atom substituted on the above-mentioned alkyl groups. Specific preferable examples thereof include those having 1 to 6 carbon atoms, such as trifluoromethyl, trichloromethyl, tetrafluoroethyl and tetrachloroethyl groups. The alkoxy group is preferably that having 1 to 6 carbon atoms, and examples thereof include methoxy, ethoxy, n-propoxy, isopropoxy, n-butoxy, isobutoxy, sec-butoxy t-butoxy, n-pentyloxy and n-hexyloxy groups. The alkoxy—alkoxy group is preferably an alkoxyalkoxy group having 2 to 12 carbon atoms, with a $C_{1-6}$-alkoxy-$C_{1-6}$-alkoxy group being particularly preferred. Specific examples thereof include methoxymethoxy, methoxyethoxy, ethoxymethoxy, n-propoxymethoxy and n-butoxymethoxy groups. The alkoxycarbonyl group is preferably that having 2 to 7 carbon atoms, and examples thereof include methoxycarbonyl, ethoxycarbonyl, n-propoxycarbonyl, isopropyloxycarbonyl, n-butoxycarbonyl, isobutoxycarbonyl, sec-butoxycarbonyl, t-butoxycarbonyl, n-pentyloxycarbonyl and n-hexyloxycarbonyl groups. The phenyl, phenoxy, benzyloxy or dioxolanyl group, or the fused aromatic ring may be substituted. Examples of substituents on these groups or the ring include alkyl groups having 1 to 6 carbon atoms, alkoxy groups having 1 to 6 carbon atoms, halogen atoms, halogeno-$C_{1-6}$-alkyl groups, $C_{1-6}$-alkoxy-$C_{1-6}$-alkoxy groups, a tetrahydropyranyloxy group, a carboxyl group, $C_{2-7}$-alkoxycarbonyl groups, a cyano group, a hydroxyl group, a nitro group, a tetrazolyl group, and an amino group which may be substituted. Of these, alkoxy groups such as methoxy, ethoxy, n-propoxy, isopropoxy and n-butoxy groups are particularly preferred. Examples-of the amino group which may be substituted include an amino group, mono- or di-$C_{1-6}$-alkylamino groups, $C_{1-7}$-acylamino groups, $C_{1-6}$-alkanesulfonylamino groups, arylsulfonylamino groups, and a benzoylamino group which may be substituted, and examples of the substituent on the benzoylamino group include 2-phenylalkoxy, 3-phenylalkoxy and 4-phenylalkoxy groups. Specific examples of the substituted amino groups include methylamino, dimethylamino, acetamino, benzoylamino, 4-(4-phenylbutoxy)benzoylamino, methanesulfonylamino, benzenesulfonylamino and p-toluenesulfonylamino groups.

The phenyl group in the general formula (1) may include a case where $R^2$, $R^3$ and $R^4$ are all hydrogen atoms, i.e., a phenyl group itself. No particular limitation is imposed on the positions of the substituents, $R^2$, $R^3$ and $R^4$ and they may be substituted at any positions of 2- to 6-positions. Examples of positions of $R^2$, $R^3$ and $R^4$ substituted on the phenyl group, and preferred substituents include 2-fluoro, 2-chloro, 2-bromo, 2-methyl 2-ethyl, 2-isopropyl, 2-n-butyl, 2-trifluoromethyl, 2-hydroxy, 2-methoxy, 2-ethoxy, 2-methoxymethyloxy, 2-(2-tetrahydropyranyl)oxy, 2-carboxy, 2-methoxycarbonyl, 2-ethoxycarbonyl, 2-isopropoxycarbonyl, 2-cyano, 2-nitro, 2-tetrazolyl, 2-phenoxy, 2-benzyloxy, 2-(4-methoxybenzyl)oxy, 2-amino, 2-dimethylamino, 2-acetamino, 2-benzoylamino, 2-(4-(4-phenylbutoxy)benzoyl)amino and 2-methanesulfonylamino groups; 3-fluoro, 3-chloro, 3-bromo, 3-methyl, 3-ethyl, 3-isopropyl, 3-t-butyl, 3-trifluoromethyl, 3-hydroxy, 3-methoxy, 3-ethoxy, 3-methoxymethyloxy, 3-(2-tetrahydropyranyl)oxy, 3-carboxy, 3-methoxycarbonyl, 3-ethoxycarbonyl, 3-isopropoxycarbonyl, 3-cyano, 3-acetyl, 3-(2-methyl-1,3-dioxolan-2-yl), 3-nitro, 3-tetrazolyl, 3-phenoxy, 3-benzyloxy, 3-(4-methoxybenzyl)oxy, 3-amino, 3-dimethylamino, 3-acetamino, 3-benzoylamino, 3-(4-(4-phenylbutoxy)benzoyl)amino and 3-methanesulfonylamino groups; 4-fluoro, 4-chloro, 4-bromo, 4-methyl, 4-ethyl, 4-isopropyl, 4-t-butyl, 4-trifluoromethyl, 4-hydroxy, 4-methoxy, 4-ethoxy, 4-methoxymethyloxy, 4-(2-tetrahydropyranyl)oxy, 4-carboxy, 4-methoxycarbonyl, 4-ethoxycarbonyl, 4-isopropoxycarbonyl, 4-cyano, 4-nitro, 4-tetrazolyl, 4-phenoxy, 4-benzyloxy, 4-(4-methoxybenzyl)oxy, 4-amino, 4-dimethylamino, 4-acetamino, 4-benzoylamino, 4-(4-(4-phenylbutoxy)benzoyl)amino and 4-methanesulfonylamino groups; 2-hydroxy-3-nitro, 2-hydroxy-3-amino, 2-hydroxy-3-acetamino, 2-hydroxy-3-benzoylamino, 2-hydroxy-3-(4-(4-phenylbutoxy)benzoyl) amino and 2-hydroxy-3-methanesulfonylamino groups; 2,4-dichloro, 2,4-dimethyl, 2,4-dihydroxy, 2,4-dimethoxy, 2,4-diethoxy, 2,4-bis-(methoxymethyloxy), 2,4-dibenzyloxy, 2-hydroxy-4-fluoro, 2-hydroxy-4-chloro, 2-hydroxy-4-bromo, 2-hydroxy-4-methoxy, 2-hydroxy-4-benzyloxy, 4-carboxy-2-hydroxy, 4-ethoxycarbonyl-2-hydroxy, 2-hydroxy-4-methoxy-carbonyl, 2-ethoxy-4-methoxy, 4-methoxy-2-methoxymethyloxy, 4-methoxy-2-(2-tetrahydropyranyl)oxy, 2-benzyloxy-4-methoxy and 2-(4-methoxybenzyl)oxy-4-methoxy groups; 2,5-dichloro, 2,5-dimethyl, 2,5-dihydroxy, 2,5-dimethoxy, 2,5-diethoxy, 2,5-bis(methoxymethyloxy), 2-hydroxy-5-methyl, 2-hydroxy-5-cyclohexyl, 2-hydroxy-5-phenyl, 2-hydroxy-5-fluoro, 2-hydroxy-5-chloro, 2-hydroxy-5-bromo, 2-hydroxy-5-nitro, 2-hydroxy-5-methoxy, 2-hydroxy-5-ethoxy, 2-hydroxy-5-isopropoxy, 2-hydroxy-5-n-butoxy, 2-hydroxy-5-benzyloxy, 2-ethoxy-5-methoxy, 5-ethoxy-2-methoxy, 5-methoxy-2-methoxymethyloxy, 5-methoxy-2-(2-tetrahydropyranyl)oxy, 5-carboxy-2-hydroxy, 2-hydroxy-5-methoxycarbonyl, 5-ethoxycarbonyl-2-hydroxy, 5-cyano-2-hydroxy, 2-hydroxy-5-tetrazolyl, 2-hydroxy-5-amino, 2-hydroxy-5-acetamino, 2-hydroxy-5-benzoylamino, 2-hydroxy-5-(4-(4-phenylbutoxy)benzoyl)amino and 2-hydroxy-5-methanesulfonylamino groups; 2,6-difluoro, 2,6-dichloro, 2,6-dibromo, 2,6-dimethyl, 2,6-di-trifluoromethyl, 2,6-dimethoxy and 2-hydroxy-6-methoxy groups; 3,4-dichloro, 3,4-dihydroxy, 3,4-dimethoxy 3,4-bis(methoxymethyloxy), 3,4-dibenzyloxy, 3-hydroxy-4-methoxy, 4-methoxy-3-methoxymethyoxy, 4-methoxy-3-(2-tetrahydropyranyl)oxy, 4-hydroxy-3-methoxy, 3-methoxy-4-methoxymethyloxy, 3-methoxy-4-(2-tetrahydropyranyl)oxy, 3-benzyloxy-4-methoxy, 4-benzyloxy-3-methoxy, 3-methoxy-4-(4-methoxybenzyl)oxy and 4-methoxy-3-(4-methoxybenzyl)oxy groups; 3,5-dichloro, 3,5-dimethyl and 3,5-dimethoxy groups; 2,4,6-trimethyl, 2,4,6-trihydroxy and 2,4,6-trimethoxy groups; and a 3,4,5-trimethoxy group. Examples of imidazole derivatives having the fused aromatic ring formed by $R^3$ and $R^4$ in $R^2$, $R^3$ and $R^4$ together with the benzene ring include 2-[3-oxo-3-(2-(1-$R^2$-naphthyl))-1-propenyl]imidazole derivatives and 2-[3-oxo-3-(1-(2-$R^2$-naphthyl))-1-propenyl]imidazole derivatives.

In the imidazole derivatives (1) or the salts thereof according to the present invention, geometrical isomers based on substituents of a double bond exist. Besides, they may be present in the form of solvates typified by hydrates. However, all these compounds are included in the present invention.

Since the imidazole derivatives (1) according to the present invention vary in dissociation ion, salts thereof include hydrochlorides, nitrates, hydrobromides, p-toluenesulfonates, methanesulfonates, fumarates, maleates, malonates, succinates, citrates, tartrates and the like in the case where the imidazole derivatives (1) are basic compounds, and include sodium salts, potassium salts and ammonium salts in the case where the imidazole derivatives 1) are acidic compounds.

A compound in which $R^1$, $R^2$, $R^3$ and $R^4$ in the general formula (1) are all hydrogen atoms is described as Comparative Example 3 [Compound (11)] in Japanese Patent Application Laid-Open No. 36069/1995. However, this publication only describes this compound as having no non-linear optical characteristics and does not describe anything about its pharmacological effect.

The imidazole derivatives (1) according to the present invention are derived, for example, in accordance with a preparation process in which commercially available 2-imidazole carbaldehyde (2) and one of various acetophenone derivatives (3) are subjected to cross aldol condensation into a compound (1) according to the present invention as shown in the following scheme:

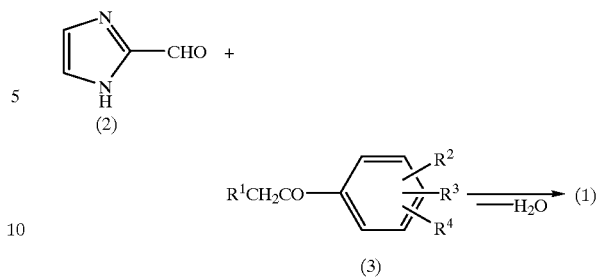

wherein $R^1$, $R^2$, $R^3$ and $R^4$ have the same meanings as defined above.

This reaction is allowed to progress in the presence of a base. As a representative process thereof, this reaction is easily carried out at 0° C. to room temperature using a dilute aqueous solution of sodium hydroxide or potassium hydroxide (or in its mixture with a lower alcohol in some cases), or at room temperature to a reflux temperature using barium hydroxide in methanol. A process in which the reaction is conducted at 0° C. to a reflux temperature using sodium methoxide in a methanol solvent or sodium ethoxide in an ethanol solvent is also preferred. Besides, a process in which a compound (1) according to the present invention is obtained by distilling off water formed at a reflux temperature using a catalytic amount of piperidine-acetic acid, piperidine-benzoic acid or the like in a solvent such as benzene or toluene is also effective. The compounds (1) according to the present invention can be obtained with good efficiency by properly using the above-described reaction conditions according to the kinds of the substituents, $R^1$ to $R^4$.

In the compounds (1) according to the present invention, a compound (1a) in which at least one of $R^2$ to $R^4$ is a hydroxyl group protected by a protecting group (a methoxymethyloxy group, a 2-tetrahydropyranyloxy group, a benzyloxy group which may be substituted, or the like) is subjected to deprotecting, thereby obtaining a compound (1b) according to the present invention, in which at least one of $R^{2a}$ to $R^{4a}$ is a hydroxyl group.

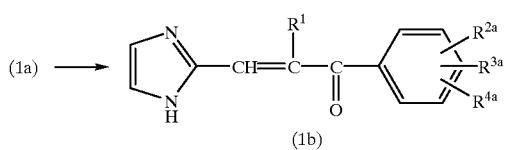

wherein $R^1$ has the same meaning as defined above, at least one of $R^{2a}$ to $R^{4a}$ is a hydroxyl group, and the others thereof are the same as their corresponding $R^2$ to $R^4$.

This reaction is carried out at room temperature to a reflux temperature using trifluoroacetic acid or diluted acetic acid in the case where a methoxymethyloxy group is present at any one of $R^2$ to $R^4$, or using p-toluenesulfonic acid monohydrate or diluted hydrochloric acid in a lower alcohol solvent in the case where a 2-tetrahydropyranyloxy group is present at any one of $R^2$ to $R^4$, or using a mixture of concentrated hydrochloric acid and acetic acid in the case where a benzyloxy group which may be substituted is present at any one of $R^2$ to $R^4$.

In the compounds (1) according to the present invention, a compound (1c) in which at least one of $R^2$ to $R^4$ is a carboxyl group is esterified, thereby obtaining a compound (1d) according to the present invention, in which at least one of $R^{2b}$ to $R^{4b}$ is an alkoxycarbonyl group.

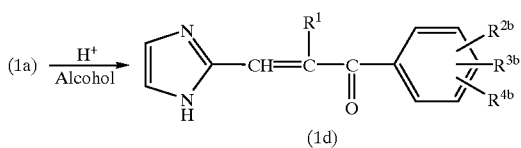

wherein $R^1$ has the same meaning as defined above, at least one of $R^{2b}$ to $R^{4b}$ is an alkoxycarbonyl group, and the others thereof are the same as their corresponding $R^2$ to $R^4$.

This esterification reaction is carried out at room temperature to a reflux temperature using a lower alcohol under acid conditions of hydrochloric acid, sulfuric acid or the like, which the process is most widely used.

The imidazole derivatives (1) according to the present invention may also be derived, for example, in accordance with a preparation process in which a 2-imidazole carbaldehyde derivative (4) having a protecting group at a 1-position, which is described in the following literature, and one of various acetophenone derivatives (3) are subjected to cross aldol condensation into a compound (5), and the compound (5) is then subjected to deprotecting into a compound (1) according to the present invention.

Literature:
  Kirk, K. L., J. Org. Chem., 43, 4381 (1978);
  Whitten, J. P., Matthews, D. P., and McCarthy, J. R., J. Org. Chem., 51, 1891 (1986); and
  Carpenter, A. J., and Chadwick, D. J., Tetrahedron, 42, 2351 (1986).

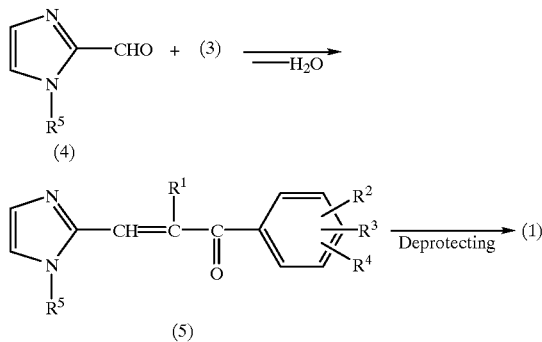

wherein $R^1$, $R^2$, $R^3$ and $R^4$ have the same meanings as defined above, and $R^5$ is a triphenylmethyl, 2-(trimethylsilyl)-ethoxymethyl or dimethylsulfamoyl group.

The reaction in which the compound (5) is obtained from the 2-imidazole carbaldehyde derivative (4) having a protecting group at a 1-position is allowed to progress in the presence of a base. As a representative process thereof, this reaction is easily carried out at 0° C. to room temperature using a dilute aqueous solution of sodium hydroxide or potassium hydroxide (or in its mixture with a lower alcohol in some cases), or at room temperature to a reflux temperature using sodium methoxide in a methanol solvent.

Conditions for deprotecting the compound (5) vary according to the kind of the protecting group. The deprotecting is conducted at room temperature to 50° C. using 10 to 35% hydrochloric acid in methanol in the case where the compound (5) has a triphenylmethyl group as $R^5$, or at room temperature to a reflux temperature using a 1 M tetrahydrofuran (THF) solution of tetrabutylammonium fluoride [(n-Bu)$_4$NF] in the case where the compound (5) has a 2-(trimethylsilyl)ethoxymethyl group as $R^5$, or at a reflux temperature using a 10% aqueous solution of sulfuric acid in the case where the compound (5) has a dimethylsulfamoyl group as $R^5$, whereby a compound (1) according to the present invention can be obtained with good efficiency.

The isolation of the compound (1) according to the present invention from the final reaction mixture in each of the above-described reactions may be generally conducted in accordance with methods known per se in the art, for example, means such as extraction with solvent, recrystallization, column chromatography and/or the like.

The compounds (1) can be formulated into medicinal compositions in various forms such as tablets, granules, powder, capsules, suspensions, injections, suppositories and preparations for external application by blending a pharmaceutically acceptable carrier in accordance with a method known per se in the art. In order to prepare, for example, a solid preparation, it is preferred that an excipient, and optionally a binder, disintegrator, extender, coating agent, sugar coating agent and/or the like be added to the compound (1), and the mixture be then formed into tablets, granules, capsules, suppositories or the like in accordance with a method known per se in the art. In a case where an injection is prepared, it is only necessary to dissolve, disperse or emulsify the compound (1) in an aqueous carrier such as distilled water for injection in advance to formulate a liquid preparation, or to formulate the compound (1) into powder for injection which is dissolved upon its use. Examples of an administration method of an injection preparation include intravenous administration, intraarterial administration, intraperitoneal administration, subcutaneous administration and drip infusion.

Diseases of patients to which the medicine according to the present invention is administered include diseases based on the production of cytokine and diseases caused by immune function disorder. Specific examples thereof include rejection upon organ transplantation; autoimmune diseases such as allergy, atopy and rheumatism; bronchial asthma; IgA nephropathy; osteoporosis; inflammation; cancer; and HIV infection.

The dose of the medicine according to the present invention in such a case varies according to the administration route thereof, and the condition, age, sex and the like of a patient to be administered. However, it is normally preferred to administer the medicine in a dose of 0.001 to 10 mg/kg, particularly, 0.01 to 1 mg/kg in terms of the imidazole derivative or the salt thereof at once or in several portions a day for an adult in the case of oral administration.

The present invention will hereinafter be described by the following examples. However, the present invention is not limited to these examples. Incidentally, "Me", "Et", "Ph", "Bn", "THP" and "Ac", which will be used in the following examples, are abbreviations for methyl, ethyl, phenyl, benzyl, tetrahydro-2-pyranyl and acetyl groups, respectively.

EXAMPLE 1

Synthesis of 2-[(E)-3-oxo-3-(3-methoxyphenyl)-1-propenyl]imidazole {in the formula (1), $R^1$=H, $R^2$=3-OMe, $R^3$=$R^4$=H}:

2-Imidazole carbaldehyde (2) (2.88 g, 30 mmol) and 3'-methoxyacetophenone (5.40 g, 36 mmol) were dissolved in 40 ml of ethanol, and a 1N aqueous solution (40 ml) of sodium hydroxide was added to the solution. The mixture was stirred at room temperature for 8 hours. 1N Hydrochloric acid (40 ml) was added to the resultant reaction mixture to conduct extraction with chloroform. An organic layer was washed with saturated brine, dried and then concentrated under reduced pressure. The resultant residue was subjected to column chromatography on silica gel. Crystals obtained from a fraction eluted with 1% (v/v) methanol-chloroform were recrystallized from ethyl acetate to obtain 3.25 g (yield: 48%) of the title compound.

Melting point: 187 to 189° C.; $^1$H-NMR δ ppm (DMSO-$d_6$): 3.86(3H,s), 7.23–7.35(3H,m), 7.49(1H,d,J=15.0 Hz), 7.51–7.54(2H,m), 7.63(1H,d,J=8.0 Hz), 7.81(1H,d,J=15.0 Hz), 12.79(1H,s).

EXAMPLE 2

The following compound was obtained in the same manner as in Example 1 except that 2-imidazole carbaldehyde (2) and 2'-methoxyacetophenone were used.

2-[(E)-3-Oxo-3-(2-methoxyphenyl)-1-propenyl]-imidazole {in the formula (1), $R^1$=H, $R^2$=2-OMe, $R^3$=$R^4$=H}

Melting point: 143 to 144° C.; $^1$H-NMR δ ppm (CDCl$_3$): 3.82(3H,s), 6.96(1H,d,J=8.0 Hz), 7.01(1H,t,J=8.0 Hz), 7.10–7.32(2H,br), 7.47(1H,dt,J=8.0,2.0 Hz), 7.59(1H,dd,J=8.0,2.0 Hz), 7.64(2H,s), 11.36(1H,s).

EXAMPLE 3

The following compound was obtained in the same manner as in Example 1 except that 2-imidazole carbaldehyde (2) and 2',5'-dimethoxyacetophenone were used.

2-[(E)-3-Oxo-3-(2,5-dimethoxyphenyl)-1-propenyl]-imidazole {in the formula (1), $R^1$=H, $R^2$=2-OMe, $R^3$=5-OMe, $R^4$=H}

Melting point: 212 to 214° C.; $^1$H-NMR δ ppm (CDCl$_3$): 3.79(6H,s), 6.90(1H,d,J=9.3 Hz), 7.02(1H,dd,J=9.3,2.9 Hz), 7.16(1H,d,J=2.9 Hz), 7.23(2H,s), 7.61(1H,d,J=15.0 Hz), 7.67(1H,d,J=15.0 Hz).

EXAMPLE 4

The following compound was obtained in the same manner as in Example 1 except that 2-imidazole carbaldehyde (2) and 2',4'-dimethoxyacetophenone were used.

2-[(E)-3-Oxo-3-(2,4-dimethoxyphenyl)-1-propenyl]-imidazole {in the formula (1), $R^1$=H, $R^2$=2-OMe, $R^3$=$R^4$-OMe, $R^4$=H}

Melting point: 152 to 154° C.; $^1$H-NMR δ ppm (CDCl$_3$): 3.87(3H,s), 3.88(3H,s), 6.48(1H,d,J=2.0 Hz), 6.55(1H,dd,J=8.0,2.0 Hz), 7.22(2H,br), 7.65(1H,d,J=15.0 Hz), 7.77(1H,d,J=8.0 Hz), 7.78(1H,d,J=15.0 Hz), 10.40(1H,br).

EXAMPLE 5

The following compound was obtained in the same manner as in Example 1 except that 2-imidazole carbaldehyde (2) and 2'-hydroxyacetophenone were used.

2-[(E)-3-Oxo-3-(2-hydroxyphenyl)-1-propenyl]-imidazole {in the formula (1), $R^1$=H, $R^2$=2-OH, $R^3$=$R^4$=H}

Melting point: 184 to 185° C.; $^1$H-NMR δ ppm (DMSO-$d_6$): 6.99–7.05(2H,m), 7.15–7.45(2H,br), 7.53–7.60(2H,m), 7.93(1H,d,J=15.0 Hz), 7.98(1H,d,J=8.0 Hz), 12.29(1H,s), 12.84(1H,s).

EXAMPLE 6

The following compound was obtained in the same manner as in Example 1 except that 2-imidazole carbaldehyde (2) and 3',5'-dimethoxyacetophenone were used.

2-[(E)-3-Oxo-3-(3,5-dimethoxyphenyl)-1-propenyl]-imidazole {in the formula (1), $R^1$=H, $R^2$=3-OMe, $R^3$=5-OMe, $R^4$=H}

Melting point: 222 to 224° C.; $^1$H-NMR δ ppm (CDCl$_3$): 3.86(6H,s), 6.68(1H,t,J=2.0 Hz), 7.19(2H,d,J=2.0 Hz), 7.30(2H,br), 7.63(1H,d,J=15.0 Hz), 7.79(1H,d,J=15.0 Hz), 9.60(1H,br).

EXAMPLE 7

The following compound was obtained in the same manner as in Example 1 except that 2-imidazole carbaldehyde (2) and 2',6'-dimethoxyacetophenone were used 2-[(E)-3-Oxo-3-(2,6-dimethoxyphenyl)-1-propenyl]-imidazole {in the formula (1), $R^1$=H, $R^2$=2-OMe, $R^3$=6-OMe, $R^4$=H}

Melting point: 150 to 151° C.; $^1$H-NMR δ ppm (CDCl$_3$): 3.74(6H,s), 6.59(2H,d,J=8.0 Hz), 7.13(1H,d,J=16.0 Hz), 7.25(2H,br), 7.32(1H,t,J=8.0 Hz), 7.33(1H,d,J=16.0 Hz), 11.20(1H,br).

EXAMPLE 8

The following compound was obtained in the same manner as in Example 1 except that 2-imidazole carbaldehyde (2) and 4'-methoxyacetophenone were used.

2-[(E)-3-Oxo-3-(4-methoxyphenyl)-1-propenyl]-imidazole {in the formula (1), $R^1$=H, $R^2$=4-OMe, $R^3$=$R^4$=H}

Melting point: 196.5 to 197.5° C.; $^1$H-NMR δ ppm (DMSO-$d_6$): 3.88(3H,s), 7.11(2H,d,J=9.0 Hz), 7.28(2H,br), 7.47(1H,d,J=15.0 Hz), 7.86(1H,d,J=15.0 Hz), 8.04(2H,d,J=9.0 Hz), 12.75(1H,br).

EXAMPLE 9

The following compound was obtained in the same manner as in Example 1 except that 2-imidazole carbaldehyde (2) and 4'-(tetrahydro-2-pyranyl)oxy-acetophenone were used.

2-[(E)-3-Oxo-3-(4-(tetrahydro-2-pyranyl)oxyphenyl)-1-propenyl]imidazole {in the formula (1), $R^1$=H, $R^2$=4-OTHP, $R^3$=$R^4$=H}

Melting point: 174 to 176° C.; $^1$H-NMR δ ppm (CDCl$_3$): 1.52–2.20(6H,m), 3.60–3.90(2H,m), 5.51(1H,t,J=3.0 Hz), 7.08(2H,d,J=9.0 Hz), 7.28(2H,s), 7.82(1H,d,J=15.0 Hz), 7.92(1H,d,J=15.0 Hz), 7.97(2H,d,J=9.0 Hz).

EXAMPLE 10

The following compound was obtained in the same manner as in Example 1 except that 2-imidazole carbaldehyde (2) and 4'-chloroacetophenone were used.

2-[(E)-3-Oxo-3-(4-chlorophenyl)-1-propenyl]imidazole {in the formula (1), $R^1$=H, $R^2$=4-Cl, $R^3$=$R^4$=H}

Melting point: 202.5 to 204.5° C.; $^1$H-NMR δ ppm (DMSO-$d_6$): 7.30(2H,br), 7.50(1H,d,J=15.0 Hz), 7.65(2H,d,J=8.0 Hz), 7.82(1H,d,J=15.0 Hz), 8.04(2H,d,J=8.0 Hz), 12.81(1H,s).

EXAMPLE 11

The following compound was obtained in the same manner as in Example 1 except that 2-imidazole carbaldehyde (2) and 2'4'-dichloroacetophenone were used.

2-[(E)-3-Oxo-3-(2,4-dichlorophenyl)-1-propenyl]imidazole {in the formula (1), $R^1$=H, $R^2$=2-Cl, $R^3$=4-Cl, $R^4$=H}

Melting point: 200.5 to 202° C.; $^1$H-NMR δ ppm (CDCl$_3$): 7.21(2H,br), 7.28(1H,d,J=16.0 Hz), 7.32(1H,br), 7.35(1H,dd,J=8.0,2.0 Hz), 7.39(1H,d,J=16.0 Hz), 7.46(1H,d,J=8.0 Hz), 9.62(1H,br).

EXAMPLE 12

The following compound was obtained in the same manner as in Example 1 except that 2-imidazole carbaldehyde (2) and 2'-trifluoromethylacetophenone were used.

2-[(E)-3-Oxo-3-(2-trifluoromethylphenyl)-1-propenyl] imidazole {in the formula (1), $R^1$=H, $R^2$=2-$CF_3$, $R^3$=$R^4$=H} $^1$H-NMR δ ppm (CDCl$_3$): 7.16–7.32(2H,br), 7.29(1H,d, J=16.0 Hz), 7.44(1H,d,J=16.0 Hz), 7.49–7.54(1H,m), 7.60–7.65(2H,m), 7.76–7.80(1H,m), 11.42(1H,s).

EXAMPLE 13

The following compound was obtained in the same manner as in Example 1 except that 2-imidazole carbaldehyde (2) and 3'-chloroacetophenone were used.

2-[(E)-3-Oxo-3-(3-chlorophenyl)-1-propenyl]imidazole {in the formula (1), $R^1$=H, $R^2$=3-Cl, $R^3$=$R^4$=H}

Melting point: 182 to 183° C.; $^1$H-NMR δ ppm (DMSO-d$_6$): 7.32(2H,s), 7.51(1H,d,J=15.0 Hz), 7.63(1H,t,J=8.0 Hz), 7.72–7.76(1H,m), 7.81(1H,d,J=15.0 Hz), 7.97–8.03(2H,m), 12.82(1H,br).

EXAMPLE 14

The following compound was obtained in the same manner as in Example 1 except that 2-imidazole carbaldehyde (2) and 2'-methylacetophenone were used.

2-[(E)-3-Oxo-3-(2-methylphenyl)-1-propenyl]imidazole {in the formula (1), $R^1$=H, $R^2$=2-Me, $R^3$=$R^4$=H}

Melting point: 134 to 135° C.; $^1$H-NMR δ ppm (CDCl$_3$): 7.10(1H,d,J=16.0 Hz), 7.17(1H,d,J=16.0 Hz), 7.30(2H,s), 7.47–7.62(4H,m), 12.76(1H,br).

EXAMPLE 15

The following compound was obtained in the same manner as in Example 1 except that 2-imidazole carbaldehyde (2) and 2'-chloroacetophenone were used.

2-[(E)-3-Oxo-3-(2-chlorophenyl)-1-propenyl]imidazole {in the formula (1), $R^1$=H, $R^2$=2-Cl, $R^3$=$R^4$=H}

Melting point: 141.5 to 142.5° C.; $^1$H-NMR δ ppm (DMSO-d$_6$): 7.10(1H,d,J=16.0 Hz), 7.17(1H,d,J=16.0 Hz), 7.30(2H,s), 7.47–7.62(4H,m), 12.76(1H,br).

EXAMPLE 16

The following compound was obtained in the same manner as in Example 1 except that 2-imidazole carbaldehyde (2) and 2'-ethoxyacetophenone were used.

2-[(E)-3-Oxo-3-(2-ethoxyphenyl)-1-propenyl]imidazole {in the formula (1), $R^1$=H, $R^2$=2-OEt, $R^3$=$R^4$=H}

Melting point: 138 to 139° C.; $^1$H-NMR δ ppm (CDCl$_3$): 1.33(3H,t,J=7.0 Hz), 4.04(2H,q,J=7.0 Hz), 6.92(1H,d,J=8.0 Hz), 6.99(1H,t,J=8.0 Hz), 7.20(2H,s), 7.40–7.46(1H,m), 7.55(1H,dd,J=8.0,2.0 Hz), 7.60(1H,d,J=16.0 Hz), 7.65(1H, d,J=16.0 Hz), 11.91(1H,br).

EXAMPLE 17

The following compound was obtained in the same manner as in Example 1 except that 2-imidazole carbaldehyde (2) and 2'-ethoxy-4'-methoxyacetophenone were used.

2-[(E)-3-Oxo-3-(2-ethoxy-4-methoxyphenyl)-1-propenyl]imidazole {in the formula (1), $R^1$=H, $R^2$=2-OEt, $R^3$=4-OMe, $R^4$=H}

Melting point: 170 to 171° C.; $^1$H-NMR δ ppm (CDCl$_3$): 1.35(3H,t,J=7.0 Hz), 3.84(3H,s), 4.16(2H,q,J=7.0 Hz), 6.63 (1H,dd,J=8.0,2.0 Hz), 6.66(1H,d,J=2.0 Hz), 7.15(2H,s), 7.30(1H,d,J=16.0 Hz), 7.57(1H,d,J=8.0 Hz), 7.62(1H,d,J=16.0 Hz), 12.60(1H,br).

EXAMPLE 18

The following compound was obtained in the same manner as in Example 1 except that 2-imidazole carbaldehyde (2) and 4'-carboxyacetophenone were used.

2-[(E)-3-Oxo-3-(4-carboxyphenyl)-1-propenyl]-imidazole {in the formula (1), $R^1$=H, $R^2$=4-$CO_2$H, $R^3$=$R^4$=H}

Melting point: >290° C.; $^1$H-NMR δ ppm (DMSO-d$_6$): 7.32(2H,s), 7.51(1H,d,J=16.0 Hz), 7.84(1H,d,J=16.0 Hz), 8.11(4H,s).

EXAMPLE 19

The following compound was obtained in the same manner as in Example 1 except that 2-imidazole carbaldehyde (2) and propiophenone were used.

2-((E)-2-Methyl-3-oxo-3-phenyl-1-propenyl)imidazole {in the formula (1), $R^1$=Me, $R^2$=$R^3$=$R^4$=H}

Melting point: 127 to 128.5° C.; $^1$H-NMR δ ppm (CDCl$_3$): 2.49(3H,d,J=1.5 Hz), 6.94(1H,d,J=1.5 Hz), 7.21 (2H,s), 7.39–7.45(2H,m), 7.49–7.55(1H,m), 7.64–7.69(2H, m).

EXAMPLE 20

The following compound was obtained in the same manner as in Example 1 except that 2-imidazole carbaldehyde (2) and 2'-nitroacetophenone were used.

2-[(E)-3-Oxo-3-(2-nitrophenyl)-1-propenyl]imidazole {in the formula (1), $R^1$=H, $R^2$=2-$NO_2$, $R^3$=$R^4$=H}

Melting point: 175 to 176° C.; $^1$H-NMR δ ppm (DMSO-d$_6$): 7.06(1H,d,J=16.0 Hz), 7.14(1H,d,J=16.0 Hz), 7.29(2H, s), 7.70(1H,dd,J=8.0,2.0 Hz), 7.81(1H,dt,J=8.0,2.0 Hz), 7.91 (1H,dt,J=8.0,2.0 Hz), 8.12(1H,dd,J=8.0,2.0 Hz), 12.73(1H, br).

EXAMPLE 21

The following compound was obtained in the same manner as in Example 1 except that 2-imidazole carbaldehyde (2) and 4'-fluoroacetophenone were used.

2-[(E)-3-Oxo-3-(4-fluorophenyl)-1-propenyl]imidazole {in the formula (1), $R^1$=H, $R^2$=4-F, $R^3$=$R^4$=H}

Melting point: 172 to 173° C.; $^1$H-NMR δ ppm (DMSO-d$_6$): 7.31(2H,s), 7.38–7.44(2H,m), 7.50(1H,d,J=16.0 Hz), 7.84(1H,d,J=16.0 Hz), 8.10–8.16(2H,m), 12.79(1H,br).

EXAMPLE 22

The following compound was obtained in the same manner as in Example 1 except that 2-imidazole carbaldehyde (2) and 4'-bromoacetophenone were used.

2-[(E)-3-Oxo-3-(4-bromophenyl)-1-propenyl]imidazole {in the formula (1), $R^1$=H, $R^2$=4-Br, $R^3$=$R^4$=H}

Melting point: 208 to 210° C.; $^1$H-NMR δ ppm (DMSO-d$_6$): 7.31(2H,s), 7.50(1H,d,J=16.0 Hz), 7.78–7.84(3H,m), 7.95–7.99(2H,m), 12.80(1H,br).

EXAMPLE 23

Synthesis of 2-[(E)-3-oxo-3-(4-hydroxyphenyl)-1-propenyl]imidazole {in the formula (1), $R^1$=H, $R^2$=4-OH, $R^3$=$R^4$=H}:

2-[(E)-3-Oxo-3-(4-(tetrahydro-2-pyranyl)oxyphenyl)-1-propenyl]imidazole {in the formula (1), $R^1$=H, $R^2$=4-OTHP, $R^3$=$R^4$=H} (0.60 g, 2.0 mmol) obtained in Example 9 was dissolved in 8 ml of methanol, and p-toluenesulfonic acid monohydrate (0.42 g, 2.2 mmol) was added to the solution. The mixture was stirred at room temperature for 3 hours. The resultant reaction mixture was dried to solid under reduced pressure, and a 3% aqueous solution (10 ml) of sodium hydrogencarbonate was added to the residue. Crystals deposited were collected by filtration and dried. The thus-obtained crystals were recrystallized from a mixed solution of acetone and ethyl acetate to obtain 0.33 g (yield: 77%) of the title compound.

Melting point: 265 to 267° C. (decomposed). $^1$H-NMR δ ppm (DMSO-$d_6$): 6.92(2H,d,J=9.0 Hz), 7.28(2H,s), 7.44 (1H,d,J=15.0 Hz), 7.84(1H,d,J=15.0 Hz), 7.95(2H,d,J=9.0 Hz), 10.38(1H,s).

EXAMPLE 24

Synthesis of 2-[(E)-3-oxo-3-(4-ethoxycarbonylphenyl)-1-propenyl]imidazole {in the formula (1), $R^1$=H, $R^2$=4-$CO_2$Et, $R^3$=$R^4$=H}:

2-[(E)-3-Oxo-3-(4-carboxyphenyl)-1-propenyl]imidazole {in the formula (1), $R^1$=H, $R^2$=4-$CO_2$H, $R^3$=$R^4$=H} (0.24 g, 1.0 mmol) obtained in Example 18 was dissolved in 10 ml of ethanol, and concentrated sulfuric acid (3 drops) was added to the solution. The mixture was heated and refluxed for 8 hours. The resultant reaction mixture was dried to solid under reduced pressure, and a saturated aqueous solution (5 ml) of sodium hydrogencarbonate was added to the residue to conduct extraction with chloroform. An organic layer was dried and then concentrated under reduced pressure. Crystals deposited were recrystallized from a mixed solution of chloroform and hexane to obtain 0.14 g (yield: 52%) of the title compound.

Melting point: 174 to 175° C.; $^1$H-NMR δ ppm (DMSO-$d_6$): 1.36(3H,t,J=7.0 Hz), 4.37(2H,q,J=7.0 Hz), 7.34(2H,br), 7.52(1H,d,J=16.0 Hz), 7.83(1H,d,J=16.0 Hz), 8.13(4H, s), 12.84(1H,br).

EXAMPLE 25

The following compound was obtained in the same manner as in Example 1 except that 2-imidazole carbaldehyde (2) and 3'-methoxymethyloxyacetophenone were used.

2-[(E)-3-Oxo-3-(3-methoxymethyloxyphenyl)-1-propenyl]imidazole {in the formula (1), $R^1$=H, $R^2$=3-$OCH_2$OMe, $R^3$=$R^4$=H}

Melting point: 174 to 175° C.; $^1$H-NMR δ ppm (DMSO-$d_6$): 3.41(3H,s), 5.28(2H,s), 7.25–7.36(3H,m), 7.47–7.55 (2H,m), 7.61–7.65(1H,m), 7.67–7.71(1H,m), 7.81(1H,d,J= 16.0 Hz), 12.80(1H,br).

EXAMPLE 26

The following compound was obtained in the same manner as in Example 1 except that 2-imidazole carbaldehyde (2) and 2-methoxyacetophenone were used.

2-((Z)-2-Methoxy-3-oxo-3-phenyl-1-propenyl)imidazole {in the formula (1), $R^1$=OMe, $R^2$=$R^3$=$R^4$=H}

Melting point: 123.5 to 124.5° C.; $^1$H-NMR δ ppm ($CDCl_3$): 3.97(3H,s), 6.63(1H,s), 7.21(2H,br), 7.45–7.50 (2H,m), 7.57–7.63(1H,m), 7.83–7.87(2H,m).

EXAMPLE 27

Synthesis of 2-[(E)-3-oxo-3-(3-hydroxyphenyl)-1-propenyl]imidazole {in the formula (1), $R^1$=H, $R^2$=3-OH, $R^3$=$R^4$=H}:

2-[(E)-3-Oxo-3-(3-methoxymethyloxyphenyl)-1-propenyl]imidazole {in the formula (1), $R^1$=H, $R^2$=3-$OCH_2$OMe, $R^3$=$R^4$=H} (0.26 g, 1.0 mmol) obtained in Example 25 was suspended in 5 ml of dichloromethane, and trifluoroacetic acid (1 ml) was added to the suspension. The mixture was stirred at room temperature for 6 hours. The resultant reaction mixture was dried to solid under reduced pressure, and a 3% aqueous solution (5 ml) of sodium hydrogencarbonate was added to the residue. Crystals deposited were collected by filtration and dried. The thus-obtained crystals were recrystallized from acetone to obtain 0.11 g (yield: 52%) of the title compound.

Melting point: 246 to 248° C. (decomposed). $^1$H-NMR δ ppm (DMSO-$d_6$): 7.05–7.09(1H,m), 7.29(2H,s), 7.36–7.41 (2H,m), 7.44–7.50(2H,m), 7.78(1H,d,J=16.0 Hz), 9.78(1H, s), 12.79(1H,br).

EXAMPLE 28

The following compound was obtained in the same manner as in Example 1 except that 2-imidazole carbaldehyde (2) and 3'-methanesulfonylaminoacetophenone were used.

2-[(E)-3-Oxo-3-(3-methanesulfonylaminophenyl)-1-propenyl]imidazole {in the formula (1), $R^1$=H, $R^2$=3-$NHSO_2$Me, $R^3$=$R^4$=H}

Melting point: 191 to 192.5° C.; $^1$H-NMR δ ppm (DMSO-$d_6$): 3.04(3H,s), 7.15–7.45(2H,br), 7.48–7.58(3H,m), 7.74–7.86(3H,m), 9.94(1H,br), 12.80(1H,br).

EXAMPLE 29

The following compound was obtained in the same manner as in Example 1 except that 2-imidazole carbaldehyde (2) and 3',4'-dichloroacetophenone were used.

2-[(E)-3-Oxo-3-(3,4-dichlorophenyl)-1-propenyl] imidazole {in the formula (1), $R^1$=H, $R^2$=3-Cl, $R^3$=4-Cl, $R^4$=H}

Melting point: 164 to 165° C.; $^1$H-NMR δ ppm (DMSO-$d_6$): 7.33(2H,s), 7.52(1H,d,J=16.0 Hz), 7.80(1H,d,J=16.0 Hz), 7.86(1H,d,J=8.0 Hz), 7.99(1H,dd,J=8.0,2.0 Hz), 8.20 (1H,d.J=2.0 Hz), 12.82(1H,br).

EXAMPLE 30

The following compound was obtained in the same manner as in Example 1 except that 2-imidazole carbaldehyde (2) and 2',5'-dichloroacetophenone were used 2-[(E)-3-Oxo-3-(2,5-dichlorophenyl)-1-propenyl] imidazole {in the formula (1), $R^1$=H, $R^2$=2-Cl, $R^3$=5-Cl, $R^4$=H}

Melting point: 156 to 158° C.; $^1$H-NMR δ ppm (DMSO-$d_6$): 7.13(2H,s), 7.31(2H,s), 7.62–7.68(3H,m), 12.77(1H,br).

EXAMPLE 31

The following compound was obtained in the same manner as in Example 1 except that 2-imidazole carbaldehyde (2) and 3'-benzyloxyacetophenone were used.

2-[(E)-3-Oxo-3-(3-benzyloxyphenyl)-1-propenyl] imidazole {in the formula (1), $R^1$=H, $R^2$=3-OBn $R^3$=$R^4$=H}

Melting point: 185.5 to 186.5° C.; $^1$H-NMR δ ppm (DMSO-$d_6$): 5.21(2H,s), 7.25–7.54(10H,m), 7.61–7.66(2H, m), 7.83(1H,d,J=16.0 Hz), 12.78(1H,br).

EXAMPLE 32

The following compound was obtained in the same manner as in Example 1 except that 2-imidazole carbaldehyde (2) and 4'-phenoxyacetophenone were used.

2-[(E)-3-Oxo-3-(4-phenoxyphenyl)-1-propenyl] imidazole {in the formula (1), $R^1$=H, $R^2$=4-OPh, $R^3$=$R^4$=H}

Melting point: 186 to 187° C.; $^1$H-NMR δ ppm (DMSO-$d_6$): 7.10–7.53(10H,m), 7.85(1H,d,J=16.0 Hz), 8.08(2H,d,J=8.0 Hz), 12.78(1H,br).

EXAMPLE 33

The following compound was obtained in the same manner as in Example 1 except that 2-imidazole carbaldehyde (2) and 3'-(2-methyl-1,3-dioxolan-2-yl)-acetophenone were used.

2-[(E)-3-Oxo-3-(3-(2-methyl-1,3-dioxolan- 2-yl)phenyl)-1-propenyl]imidazole {in the formula (1), $R^1$=H, $R^2$=3-(2-methyl-1,3-dioxolan-2-yl), $R^3$=$R^4$=H}

Melting point: 182 to 183° C.; $^1$H-NMR δ ppm (DMSO-$d_6$): 1.61(3H,s), 3.70–3.79(2H,m), 3.99–4.08(2H,m), 7.10–7.45(2H,br), 7.50(1H,d,J=16.0 Hz), 7.58(1H,t,J=8.0 Hz), 7.71(1H,dt,J=8.0,1.5 Hz), 7.84(1H,d,J=16.0 Hz), 7.98(1H,dt,J=8.0,1.5 Hz), 8.06(1H,t,J=1.5 Hz), 12.85(1H,br).

EXAMPLE 34

The following compound was obtained in the same manner as in Example 1 except that 2-imidazole carbaldehyde (2) and 3'-benzamidoacetophenone were used.

2-[(E)-3-Oxo-3-(3-benzamidophenyl)-1-propenyl] imidazole {in the formula (1), $R^1$=H, $R^2$=3-NHCOPh, $R^3$=$R^4$=H}

Melting point: 265 to 267° C. (decomposed). $^1$H-NMR δ ppm (DMSO-$d_6$): 7.18(1H,s), 7.41(1H,s), 7.50–7.65(5H,m), 7.75–7.85(2H,m), 7.98–8.03(2H,m), 8.09–8.15(1H,m), 8.45–8.48(1H,m), 10.44(1H,s), 12.81(1H,s).

EXAMPLE 35

The following compound was obtained in the same manner as in Example 1 except that 2-imidazole carbaldehyde (2) and 2'-hydroxy-5'-nitroacetophenone were used.

2-[(E)-3-Oxo-3-(2-hydroxy-5-nitrophenyl)- 1-propenyl] imidazole {in the formula (1), $R^1$=H, $R^2$=2-OH, $R^3$=5-$NO_2$, $R^4$=H}

Melting point: 213 to 214.5° C.; $^1$H-NMR δ ppm (DMSO-$d_6$): 7.19(1H,d,J=9.0 Hz), 7.34(2H,s), 7.52(1H,d,J=15.6 Hz), 7.81(1H,d,J=15.6 Hz), 8.33(1H,dd,J=9.0,3.0 Hz), 8.62 (1H,d,J=3.0 Hz).

EXAMPLE 36

The following compound was obtained in the same manner as in Example 1 except that 2-imidazole carbaldehyde (2) and 5'-fluoro-2'-hydroxyacetophenone were used.

2-[(E)-3-Oxo-3-(5-fluoro-2-hydroxyphenyl)-1propenyl] imidazole {in the formula (1), $R^1$=H, $R^2$=2-OH, $R^3$=5-F, $R^4$=H}

Melting point: 186 to 187° C.; $^1$H-NMR δ ppm (DMSO-$d_6$): 7.04(1H,dd,J=9.0,5.0 Hz), 7.33(2H,s), 7.38–7.45(1H,m), 7.54(1H,d,J=15.0 Hz), 7.70(1H,dd,J=9.0,3.0 Hz), 7.85 (1H,d,J=15.0 Hz), 11.95(1H,s), 12.55(1H,s).

EXAMPLE 37

The following compound was obtained in the same manner as in Example 1 except that 2-imidazole carbaldehyde (2) and 5'-bromo-2'-hydroxyacetophenone were used.

2-[(E)-3-Oxo-3-(5-bromo-2-hydroxyphenyl)-1-propenyl] imidazole {in the formula (1), $R^1$=H, $R^2$=2-OH, $R^3$=5-Br, $R^4$=H}

Melting point: 232 to 234° C. (decomposed). $^1$H-NMR δ ppm (DMSO-$d_6$): 7.00(1H,d,J=9.0 Hz), 7.33(2H,s), 7.52 (1H,d,J=16.0 Hz), 7.67(1H,dd,J=9.0,3.0 Hz), 7.82(1H,d,J=16.0 Hz), 8.00(1H,d,J=3.0 Hz), 11.97(1H,s), 12.85(1H,s).

EXAMPLE 38

The following compound was obtained in the same manner as in Example 1 except that 2-imidazole carbaldehyde (2) and 2'-hydroxy-5'-methylacetophenone were used.

2-[(E)-3-Oxo-3-(2-hydroxy-5-methylphenyl)-1propenyl] imidazole {in the formula (1), $R^1$=H, $R^2$=2-OH, $R^3$=5-Me, $R^4$=H}

Melting point: 203 to 204.5° C.; $^1$H-NMR δ ppm (DMSO-$d_6$): 2.32(3H,s), 6.91(1H,d,J=8.0 Hz), 7.33(2H,s), 7.38(1H,dd,J=8.0,2.0 Hz), 7.57(1H,d,J=15.0 Hz), 7.79(1H,d,J=2.0 Hz), 7.93(1H,d,J=15.0 Hz), 12.21(1H.s), 12.66(1H,s).

EXAMPLE 39

The following compound was obtained in the same manner as in Example 1 except that 2-imidazole carbaldehyde (2) and 2'-hydroxy-5'-methoxyacetophenone were used.

2-[(E)-3-Oxo-3-(2-hydroxy-5-methoxyphenyl)-1-propenyl]imidazole {in the formula (1), $R^1$=H, $R^2$=2-OH, $R^3$=5-OMe, $R^4$=H}

Melting point: 220 to 221° C.; $^1$H-NMR δ ppm (DMSO-$d_6$): 3.80(3H,s), 6.96(1H,d,J=9.0 Hz), 7.21(1H,dd,J=9.0,3.0 Hz), 7.33(2H,s), 7.42(1H,d,J=3.0 Hz), 7.55(1H,d,J=15.0 Hz), 7.90(1H,d,J=15.0 Hz), 11.78(1H.s), 12.71(1H,s).

EXAMPLE 40

The following compound was obtained in the same manner as in Example 1 except that 2-imidazole carbaldehyde (2) and 2'-hydroxy-6'-methoxyacetophenone were used.

2-[(E)-3-Oxo-3-(2-hydroxy-6-methoxyphenyl)-1-propenyl]imidazole {in the formula (1), $R^1$=H, $R^2$=2-OH, $R^3$=6-OMe, $R^4$=H}

Melting point: 156 to 157° C.; $^1$H-NMR δ ppm (DMSO-$d_6$): 3.74(3H,s), 6.54(1H,d,J=8.0 Hz), 6.57(1H,d,J=8.0 Hz), 7.08(1H,d,J=16.0 Hz), 7.13(1H,d,J=16.0 Hz), 7.17–7.30 (3H,m), 10.33(1H,s), 12.64(1H,s).

EXAMPLE 41

The following compound was obtained in the same manner as in Example 1 except that 2-imidazole carbaldehyde (2) and 5'-chloro-2'-hydroxyacetophenone were used.

2-[(E)-3-Oxo-3-(5-chloro-2-hydroxyphenyl)-1-propenyl] imidazole {in the formula (1), $R^1$=H, $R^2$=2-OH, $R^3$=5-Cl, $R^4$=H}

Melting point: 221 to 222.5° C. (decomposed). $^1$H-NMR δ ppm (DMSO-$d_6$): 7.05(1H,d,J=9.0 Hz), 7.34(2H,s), 7.50–7.58(2H,m), 7.83(1H,d,J=15.5 Hz), 7.89(1H,d,J=3.0 Hz), 11.98(1H,s), 12.84(1H,s).

EXAMPLE 42

The following compound was obtained in the same manner as in Example 1 except that 2-imidazole carbaldehyde (2) and 2'-hydroxy-5'-(5-tetrazolyl)-acetophenone were used.

2-[(E)-3-Oxo-3-(2-hydroxy-5-(5-tetrazolyl)phenyl)-1-propenyl]imidazole {in the formula (1), $R^1$=H, $R^2$=2-OH, $R^3$=5-tetrazolyl, $R^4$=H}

Melting point: 260 to 265° C. (decomposed). $^1$H-NMR δ ppm (DMSO-$d_6$): 7.24(1H,d,J=9.0 Hz), 7.42(2H,s), 7.60

(1H,d,J=15.5 Hz), 8.00(1H,d,J=15.5 Hz), 8.18(1H,dd,J=9.0, 2.0 Hz), 8.61(1H,d,J=2.0 Hz), 12.33(1H,br).

EXAMPLE 43

The following compound was obtained in the same manner as in Example 1 except that 2-imidazole carbaldehyde (2) and 2'-hydroxy-3'-nitroacetophenone were used.

2-[(E)-3-Oxo-3-(2-hydroxy-3-nitrophenyl)-1-propenyl] imidazole {in the formula (1), $R^1$=H, $R^2$=2OH, $R^3$=3-$NO_2$, $R^4$=H}

Melting point: 155 to 160° C. (decomposed). $^1$H-NMR δ ppm (DMSO-$d_6$): 7.19(1H,t,J=8.0 Hz), 7.37(2H,s), 7.58(1H, d,J=15.5 Hz), 7.83(1H,d,J=15.5 Hz), 8.22(1H,dd,J=8.0,2.0 Hz), 8.25(1H,dd,J=8.0,2.0 Hz).

EXAMPLE 44

The following compound was obtained in the same manner as in Example 1 except that 2-imidazole carbaldehyde (2) and 2'-hydroxy-4'-methoxyacetophenone were used.

2-[(E)-3-Oxo-3-(2-hydroxy-4-methoxyphenyl)-1-propenyl]imidazole {in the formula (1), $R^1$=H, $R^2$=2-OH, $R^3$=4-OMe, $R^4$=H}

Melting point: 205 to 206° C.; $^1$H-NMR δ ppm (DMSO-$d_6$): 3.85(3H,s), 6.52(1H,d,J=2.0 Hz), 6.61(1H,dd,J=9.0,2.0 Hz), 7.32(2H,s), 7.57(1H,d,J=15.0 Hz), 7.92(1H,d,J=15.0 Hz), 7.99(1H,d,J=9.0 Hz), 13.06(2H,br).

EXAMPLE 45

The following compound was obtained in the same manner as in Example 1 except that 2-imidazole carbaldehyde (2) and 5'-carboxy-2'-hydroxyacetophenone were used.

2-[(E)-3-Oxo-3-(5-carboxy-2-hydroxyphenyl)-1-propenyl]imidazole {in the formula (1), $R^1$=H, $R^2$=2-OH, $R^3$=5-$CO_2$H, $R^4$=H}

Melting point: 231 to 233° C. (decomposed). $^1$H-NMR δ ppm (DMSO-$d_6$): 7.09(1H,d,J=9.0 Hz), 7.34(2H,s), 7.58 (1H,d,J=15.5 Hz), 7.91(1H,d,J=15.5 Hz), 8.07(1H,dd,J=9.0, 2.0 Hz), 8.51(1H,d,J=2.0 Hz), 12.89(3H,br).

EXAMPLE 46

The following compound was obtained in the same manner as in Example 1 except that 2-imidazole carbaldehyde (2) and 4'-bromo-2'-hydroxyacetophenone were used.

2-[(E)-3-Oxo-3-(4-bromo-2-hydroxyphenyl)-1-propenyl] imidazole {in the formula (1), $R^1$=H, $R^2$=2-OH, $R^3$=4-Br, R=H}

Melting point: 204 to 205.5° C.; $^1$H-NMR δ ppm (DMSO-$d_6$): 7.20–7.32(4H,m), 7.55(1H,d,J=15.6 Hz), 7.82–7.86 (1H,m), 7.84(1H,d,J=15.6 Hz).

EXAMPLE 47

The following compound was obtained in the same manner as in Example 1 except that 2-imidazole carbaldehyde (2) and 4'-benzyloxy-2'-hydroxyacetophenone were used.

2-[(E)-3-Oxo-3-(4-benzyloxy-2-hydroxyphenyl)-1-propenyl]imidazole {in the formula (1), $R^1$=H, $R^2$=2-OH, $R^3$=4-OBn, $R^4$=H}

Melting point: 195.5 to 196.5° C.; $^1$H-NMR δ ppm (DMSO-$d_6$): 5.22(2H,s), 6.61–6.62(1H,m), 6.69(1H,dd,J= 9.0,2.0 Hz), 7.32–7.47(7H,m), 7.57(1H,d,J=15.6 Hz), 7.94 (1H,d,J=15.6 Hz), 8.02(1H,d,J=9.0 Hz), 13.06(1H,br).

EXAMPLE 48

The following compound was obtained in the same manner as in Example 1 except that 2-imidazole carbaldehyde (2) and 2'-hydroxy-5'-phenylacetophenone were used.

2-[(E)-3-Oxo-3-(2-hydroxy-5-phenylphenyl)-1-propenyl] imidazole {in the formula (1), $R^1$=H, $R^2$=2-OH, $R^3$=5-Ph, $R^4$=H}

Melting point: 206 to 207° C.; $^1$H-NMR δ ppm (DMSO-$d_6$): 7.11(1H,d,J=9.0 Hz), 7.3 (2H,br), 7.37(1H,m), 7.50(2H, m), 7.60(1H,d,J=16.0 Hz), 7.70(2H,m), 7.86(1H,dd,J=9.0, 2.0 Hz), 8.01(1H,d,J=16.0 Hz), 8.18(1H,d,J=2.0 Hz), 12.5 (1H.br), 13.0(1H,br).

EXAMPLE 49

The following compound was obtained in the same manner as in Example 1 except that 2-imidazole carbaldehyde (2) and 5'-benzyloxy-2'-hydroxyacetophenone were used.

2-[(E)-3-Oxo-3-(5-benzyloxy-2-hydroxyphenyl)-1-propenyl]imidazole {in the formula (1), $R^1$=H, $R^2$=2OH, $R^3$=5-OBn, $R^4$=H}

Melting point: 174 to 174.5° C.; $^1$H-NMR δ ppm (DMSO-$d_6$): 5.12(2H,s), 6.95(1H,d,J=8.8 Hz), 7.28–7.55(9H,m), 7.56(1H,d,J=15.6 Hz), 7.92(1H,d,J=15.6 Hz), 11.7(1H,br), 12.8(1H,br).

EXAMPLE 50

The following compound was obtained in the same manner as in Example 1 except that 2-imidazole carbaldehyde (2) and 4'-chloro-2'-hydroxyacetophenone were used.

2-[(E)-3-Oxo-3-(4-chloro-2-hydroxyphenyl)-1-propenyl] imidazole hydrochloride {in the formula (1), $R^1$=H, $R^2$=2-OH, $R^3$=4-Cl, $R^4$=H}

Melting point: 207 to 209° C.; $^1$H-NMR δ ppm (DMSO-$d_6$): 7.07(1H,dd,J=8.5,2.1 Hz), 7.19(1H,d,J=2.1 Hz), 7.57 (1H,d,J=16.0 Hz), 7.84(2H,s), 8.02(1H,d,J=8.5 Hz), 8.55 (1H,d,J=16.0 Hz), 12.05(1H,s).

EXAMPLE 51

The following compound was obtained in the same manner as in Example 1 except that 2-imidazole carbaldehyde (2) and 4'-fluoro-2'-hydroxyacetophenone were used.

2-[(E)-3-Oxo-3-(4-fluoro-2-hydroxyphenyl)-1-propenyl] imidazole {in the formula (1), $R^1$=H, $R^2$=2-OH, $R^3$=4-F, $R^4$=H}

Melting point: 189 to 190.5° C.; $^1$H-NMR δ ppm (DMSO-$d_6$): 6.83–6.92(2H,m), 7.33(2H,s), 7.58(1H,d,J=15.5 Hz), 7.89(1H,d,J=15.5 Hz), 8.08(1H,dd,J=9.0,7.0 Hz), 12.74(2H, br).

EXAMPLE 52

The following compound was obtained in the same manner as in Example 1 except that 2-imidazole carbaldehyde (2) and 5'-cyclohexyl-2'-hydroxyacetophenone were used.

2-[(E)-3-Oxo-3-(5-cyclohexyl-2-hydroxyphenyl)-1-propenyl]imidazole {in the formula (1), $R^1$=H, $R^2$2-OH, $R^3$=5-cyclohexyl, $R^4$=H}

Melting point: 212 to 213.5° C.; $^1$H-NMR δ ppm (DMSO-$d_6$): 1.15–1.60(5H,m), 1.65–1.95(5H,m), 2.53(1H,m), 6.93 (1H,d,J=8.0 Hz), 7.34(2H,br), 7.44(1H,dd,J=8.0,2.0 Hz), 7.58(1H,d,J=15.0 Hz), 7.78(1H,d,J=2.0 Hz), 7.94(1H,d,J= 15.0 Hz), 12.20(1H,s), 12.9(1H,br).

EXAMPLE 53

Synthesis of 2-[(E)-3-oxo-3-(2-(1-hydroxynaphthyl))-1-propenyl]imidazole:

A 28% methanol solution (200 ml) of sodium methoxide was added to 2-imidazole carbaldehyde (2) (8.6 g, 90 mmol)

and 1'-hydroxy-2'-acetonaphthone (16.7 g, 90 mmol), and the mixture was heated and refluxed for 4 hours. After cooling, the resultant reaction mixture was poured into a 20% aqueous solution of ammonium chloride cooled with ice water, followed by stirring for 0.5 hours. Crystals deposited were collected by filtration, washed with water and recrystallized from a mixed solution of methanol and acetonitrile to obtain 13.0 g (yield: 55%) of the title compound.

Melting point: 196 to 197° C.; $^1$H-NMR δ ppm (DMSO-$d_6$): 7.25(2H,s), 7.49(1H,d,J=8.0 Hz), 7.59–7.77(3H,m), 7.94(1H,d,J=8.0 Hz), 8.03(1H,d,J=8.0 Hz), 8.10(1H,d,J= 15.5 Hz), 8.38(1H,d,J=8.0 Hz), 12.94(1H,s), 14.90(1H,s).

EXAMPLE 54

The following compound was obtained in the same manner as in Example 53 except that 2-imidazole carbaldehyde (2) and 5'-cyano-2'-hydroxyacetophenone were used.

2-[(E)-3-Oxo-3-(5-cyano-2-hydroxyphenyl)-1-propenyl] imidazole {in the formula (1), $R^1$=H, $R^2$=2-OH, $R^3$=5-CN, $R^4$=H}

Melting point: 196 to 197° C.; $^1$H-NMR δ ppm (DMSO-$d_6$): 7.16(1H,d,J=8.8 Hz), 7.33(2H,s), 7.51(1H,d,J=15.6 Hz), 7.81(1H,d,J=15.6 Hz), 7.90(1H,dd,J=9.0,2.0 Hz), 8.29 (1H,d,J=2.0 Hz), 12.6(2H,br).

EXAMPLE 55

The following compound was obtained in the same manner as in Example 24 except that 2-[(E)-3-oxo-3-( 5-carboxy-2-hydroxyphenyl)-1-propenyl]imidazole {in the formula (1), $R^1$=H, $R^2$=2-OH, $R^3$=5-$CO_2$H, $R^4$=H}obtained in Example 45 was used.

2-[(E)-3-Oxo-3-(5-ethoxyarbonyl-2-hydroxyphenyl)-1-propenyl]imidazole {in the formula (1), $R^1$=H, $R^2$=2-OH, $R^3$=5-$CO_2$Et, $R^4$=H}

Melting point: 176 to 177° C.; $^1$H-NMR δ ppm (DMSO-$d_6$): 1.34(3H,t,J=7.0 Hz), 4.33(2H,q,J=7.0 Hz), 7.11(1H,d, J=9.0 Hz), 7.33(2H,s), 7.56(1H,d,J=15.5 Hz), 7.85(1H,d,J= 15.5 Hz), 8.07(1H,dd,J=9.0,2.0 Hz), 8.44(1H,d,J=2.0 Hz), 12.47(1H,s), 12.95(1H,s).

EXAMPLE 56

Synthesis of 2-[(E)-3-oxo-3-(3-acethylphenyl)-1-propenyl]imidazole {in the formula (1), $R^1$=H, $R^2$=3-Ac, $R^3$=$R^4$=H}:

2-[(E)-3-Oxo-3-(3-(2-methyl-1,3-dioxolan-2-yl)phenyl)-1-propenyl]-imidazole {in the formula (1), $R^1$=H, $R^2$=3-(2-methyl-1,3-dioxolan-2-yl), $R^3$=$R^4$=H} (0.42 g, 1.5 mmol) obtained in Example 33 was dissolved in 20 ml of a mixed solution of acetone and water (9:1), and p-toluenesulfonic acid monohydrate (0.34 g, 1.8 mmol) was added to the solution. The mixture was stirred at 50° C. for 4 hours. The resultant reaction mixture was poured into a 3% aqueous solution (30 ml) of sodium hydrogencarbonate. Crystals deposited were collected by filtration, washed with water and dried. The thus-obtained crystals were recrystallized from ethyl acetate to obtain 0.24 g (yield: 67%) of the title compound.

Melting point: 171 to 172° C.; $^1$H-NMR δ ppm (DMSO-$d_6$): 2.68(3H,s), 7.32(2H,br), 7.54(1H,d,J=16.0 Hz), 7.75 (1H,t,J=8.0 Hz), 7.88(1H,d,J=16.0 Hz), 8.23–8.28(2H,m), 8.52(1H,t,J=2.0 Hz), 12.87(1H,s).

EXAMPLE 57

Synthesis of 2-[(E)-3-oxo-3-(2.5-dihydroxyphenyl)-1-propenyl]imidazole {in the formula (1), $R^1$=H, $R^2$=2-OH, $R^3$=5-OH, $R^4$=H}:

2-[(E)-3-Oxo-3-(5-benzyloxy-2-hydroxyphenyl)-1-propenyl]imidazole {in the formula (1), $R^1$=H, $R^2$=2-OH, $R^3$=5-OBn, $R^4$=H} (0.32 g, 1.0 mmol) obtained in Example 49 was dissolved in 4 ml of acetic acid, and concentrated hydrochloric acid (1 ml) was added to the solution. The mixture was stirred at 90° C. for 4 hours. The resultant reaction mixture was dried to solid under reduced pressure, and a saturated aqueous solution (10 ml) of sodium hydrogencarbonate was added to the residue to conduct extraction with chloroform. An organic layer was dried and concentrated under reduced pressure. Crystals deposited were recrystallized from ethyl acetate to obtain 0.15 g (yield: 65%) of the title compound.

Melting point: 201 to 203° C.; $^1$H-NMR δ ppm (DMSO-$d_6$): 6.85(1H,d,J=9.0 Hz), 7.04(1H,dd,J=9.0,3.0 Hz), 7.10–7.50(2H,br), 7.32(1H,d,J=3.0 Hz), 7.53(1H,d,J=15.5 Hz), 7.85(1H,d,J=15.5 Hz), 9.15(1H,s), 11.63(1H,s), 12.85 (1H,s).

EXAMPLE 58

The following compound was obtained in the same manner as in Example 57 except that 2-[(E)-3-oxo-3-(4-benzyloxy-2-hydroxyphenyl)-1-propenyl]imidazole {in the formula (1), $R^1$=H, $R^2$=2-OH, $R^3$=4-OBn, $R^4$=H} obtained in Example 47 was used.

2-[(E)-3-Oxo-3-(2.4-dihydroxyphenyl)-1-propenyl] imidazole {in the formula (1), $R^1$=H, $R^2$=2-OH, $R^3$=4-OH, $R^4$=H}

Melting point: 236 to 238° C.; $^1$H-NMR δ ppm (DMSO-$d_6$): 6.31(1H,d,J=2.0 Hz), 6.45(1H,dd,J=9.0,2.0 Hz), 7.32 (2H,s), 7.54(1H,d,J=15.5 Hz), 7.89(1H,d,J=15.5 Hz), 7.92 (1H,d,J=9.0 Hz), 10.72(1H,br), 12.78(1H,br), 13.24(1H,s).

EXAMPLE 59

Synthesis of 2-[(E)-3-oxo-3-(2-hydroxy-3-(4-(4-phenylbutoxy)benzamido)phenyl)-1-propenyl]imidazole {in the formula (1), $R^1$=H, $R^2$=2-OH, $R^3$=3-NHCOPh-4-O ($CH_2$)$_4$Ph, $R^4$=H}:

3'-Amino-2'-hydroxyacetophenone (1.51 g, 10 mmol) was dissolved in 50 ml of acetone, and potassium carbonate (6.90 g, 50 mmol) was added to the solution. 4-(4-Phenylbutoxy)benzoyl chloride (2.89 g, 10 mmol) was added dropwise to the mixture under stirring at 0° C., and stirring was conducted further for 3 hours. The resultant reaction mixture was poured into a 10% hydrochloric acid (100 ml) to conduct extraction with chloroform. An organic layer was washed with water, dried and then concentrated under reduced pressure. The residue was subjected to column chromatography on silica gel. Crystals obtained from a fraction eluted with chloroform were recrystallized from ethanol to obtain 2.82 g (yield: 70%) of 2-hydroxy-3-[4-(4-phenylbutoxy)benzamido)]acetophenone.

Melting point: 115 to 116° C.; $^1$H-NMR δ ppm (DMSO-$d_6$): 1.70–2.10(4H,m), 2.60–2.90(5H,m), 3.90–4.20(2H,m), 6.85–7.70(8H,m), 7.87(2H,d,J=9.0 Hz), 8.60(1H,s), 8.75 (2H,d,J=9.0 Hz), 12.98(1H,s).

The title compound (1.52 g; yield: 45%) was obtained in the same manner as in Example 53 except that 2-imidazole carbaldehyde (2) (0.67 g, 7 mmol) and 2-hydroxy-3-[4-(4-phenylbutoxy)benzamido)]acetophenone (2.82 g, 7 mmol) were used.

Melting point: 189 to 190° C.; $^1$H-NMR δ ppm (DMSO-$d_6$): 1.70–1.80(4H,m), 2.66(2H,t,J=7.0 Hz), 4.09(2H,t,J=7.0 Hz), 7.02–7.50(10H,m), 7.63(1H,d,J=15.5 Hz), 7.88(1H,dd, J=8.0,2.0 Hz), 7.93–8.02(3H,m), 8.08(1H,dd,J=8.0,2.0 Hz), 9.44(1H,s), 12.92(2H,s).

EXAMPLE 60

Synthesis of 2-[(E)-3-oxo-3-(2-aminophenyl)-1-propenyl]imidazole {in the formula (1), $R^1$=H, $R^2$=2-$NH_2$, $R^3$=$R^4$=H}:

1-Triphenylmethyl-2-imidazole carbaldehyde (4) (25.0 g, 74 mmol) and 2'-aminoacetophenone (10.0 g, 74 mmol) were suspended in 700 ml of ethanol, and a 25% aqueous solution (120 ml) of sodium hydroxide was added to the suspension, The mixture was stirred at room temperature for 12 hours. Water (3,000 ml) was added to the resultant reaction mixture, and crystals deposited were collected by filtration, washed with water and dried. The thus-obtained crystals were recrystallized from ethanol to obtain 17.6 g (yield: 52%) of 2-[(E)-3-oxo-3-(2-aminophenyl)-1-propenyl]-1-triphenylmethylimidazole.

Melting point: 142 to 144° C.; $^1$H-NMR δ ppm (DMSO-$d_6$): 6.12(2H,s), 6.54–6.60(2H,m), 6.77(1H,d,J=14.5 Hz), 6.89(1H,d,J=1.5 Hz), 7.13–7.36(17H,m), 7.73–7.80(2H,m).

2-[(E)-3-Oxo-3-(2-aminophenyl)-1-propenyl]-1-triphenylmethylimidazole (17.3 g, 38 mmol) was dissolved in 200 ml of methanol, and concentrated hydrochloric acid (15 ml) was added to the solution. The mixture was stirred at 40° C. for 2 hours. The resultant reaction mixture was poured into water (1,000 ml), and the resultant mixture was washed with chloroform (500 ml×2). A water layer was then cooled with ice water, and its pH was adjusted to 7.0 with a 25% aqueous solution of sodium hydroxide (using a pH meter). Crystals deposited were collected by filtration, washed with water and dried. The thus-obtained crystals were recrystallized from a mixed solution of isopropyl ether and ethyl acetate to obtain 4.55 g (yield: 56%) of the title compound.

Melting point: 172.5 to 173.5° C.; $^1$H-NMR δ ppm (DMSO-$d_6$): 6.61(1H,td,J=8.0,2.0 Hz), 6.80(1H,dd,J=8.0, 2.0 Hz), 7.15–7.38(5H,m), 7.40(1H,d,J=15.0 Hz), 7.85–7.89 (1H,m), 7.90(1H,d,J=15.0 Hz), 12.69(1H,s).

EXAMPLE 61

Synthesis of 2-[(E)-3-oxo-3-(3-aminophenyl)-1-propenyl]imidazole {in the formula (1), $R^1$=H, $R^2$=3-$NH_2$, $R^3$=$R^4$=H}:

2-[(E)-3-Oxo-3-(3-aminophenyl)-1-propenyl]-1-(2-trimethylsilyl)ethoxymethylimidazole (2.40 g; yield: 58%) was obtained in the same manner as in Example 1 except that 1-(2-trimethylsilyl)ethoxymethyl-2-imidazole carbaldehyde (2.71 g, 12 mmol) and 3'-aminoacetophenone (1.62 g, 12 mmol) were used.

Melting point: 105 to 106° C.; $^1$H-NMR δ ppm (CDCl$_3$): −0.03(9H,s), 0.91(2H,t,J=8.0 Hz), 3.53(2H,t,J=8.0 Hz), 3.84 (2H,s), 5.42(2H,s), 6.88–6.92(1H,m), 7.16(1H,d,J=1.0 Hz), 7.23(1H,d,J=1.0 Hz), 7.27(1H,t,J=8.0 Hz), 7.39(1H,t,J=2.0 Hz), 7.47–7.50(1H,m), 7.73(1H,d,J=16.0 Hz), 8.02(1H,d,J= 16.0 Hz).

A 1 M solution (5 ml) of (n-Bu)$_4$NF in THF was added to 2-[(E)-3-oxo-3-(3-aminophenyl)-1-propenyl]-1-(2-trimethylsilyl)ethoxymethylimidazole (0.69 g, 2.0 mmol) in an argon gas atmosphere, and the mixture was heated and refluxed for 1 hour. After cooling, the resultant reaction mixture was added to a sodium phosphate buffer (pH: 6.3; 20 ml). Crystals deposited were collected by filtration, washed with water and dried. The thus-obtained crystals were recrystallized from ethyl acetate to obtain 0.21 g (yield: 49%) of the title compound.

Melting point: 196 to 198° C.; $^1$H-NMR δ ppm (DMSO-$d_6$): 5.32(2H,br), 6.82–6.86(1H,m), 7.16–7.24(3H,m), 7.27 (2H,s), 7.43(1H,d,J=16.0 Hz), 7.73(1H,d,J=16.0 Hz), 12.66 (1H,br).

EXAMPLE 62

Synthesis of 2-[(E)-3-oxo-3-(3-(4-(4-phenylbutoxy)benzamido)phenyl)-1-propenyl]imidazole {in the formula (1), $R^1$=H, $R^2$=3-NHCOPh-4-O(CH$_2$)$_4$Ph, $R^3$=$R^4$=H}:

2-[(E)-3-Oxo-3-(3-aminophenyl)-1-propenyl]-1-(2-trimethylsilyl)ethoxymethylimidazole (1.37 g, 4.0 mmol) obtained as an intermediate in Example 61 was dissolved in dichloromethane (15 ml), and triethylamine (0.48 g, 4.8 mmol) was added to the solution. 4-(4-Phenylbutoxy) benzoyl chloride (1.27 g, 4.4 mmol) was added dropwise to the resultant mixture under stirring at 0° C., and stirring was conducted further for 2 hours. The resultant reaction mixture was washed with water, dried and then concentrated under reduced pressure. The residue was subjected to column chromatography on silica gel. Crystals obtained from a fraction eluted with chloroform were recrystallized from a mixed solution of ether and ethyl acetate to obtain 1.76 g (yield: 74%) of 2-[(E)-3-oxo-3-(3-(4-(4-phenylbutoxy) benzamido)phenyl)-1-propenyl]-1-(2-trimethylsilyl) ethoxymethylimidazole.

Melting point: 97.5 to 98.5° C.; $^1$H-NMR δ ppm (CDCl$_3$): −0.03(9H,s), 0.91(2H,t,J=8.0 Hz), 1.80–1.90(4H,m), 2.70 (2H,t,J=6.0 Hz), 3.52(2H,t,J=8.0 Hz), 4.02(2H,t,J=6.0 Hz), 5.40(2H,s), 6.94(2H,d,J=9.0 Hz), 7.15–7.32(7H,m), 7.49 (1H,t,J=6.0 Hz), 7.73(1H,d,J=15.0 Hz), 7.82–7.85(1H,m), 7.88(2H,d,J=9.0 Hz), 7.99–8.04(2H,m), 8.26(1H,dd,J=8.0, 2.0 Hz), 8.34(1H,s).

The title compound (0.44 g; yield: 47%) was obtained in the same manner as in Example 61 except that 2-[(E)-3-oxo-3-(3-(4-(4-phenylbutoxy)benzamido)phenyl)-1-propenyl]-1-(2-trimethylsilyl)ethoxymethylimidazole (1.19 g, 2.0 mmol) and a 1 M solution (5 ml) of (n-Bu)$_4$NF in THF were used.

Melting point: 194 to 196° C.; $^1$H-NMR δ ppm (DMSO-$d_6$): 1.70–1.80(4H,m), 2.66(2H,t,J=7.0 Hz), 4.09(2H,t,J=7.0 Hz), 7.06(2H,d,J=9.0 Hz), 7.15–7.45(7H,m), 7.52(1H,d,J= 16.0 Hz), 7.56(1H,t,J=8.0 Hz), 7.75(1H,d,J=8.0 Hz), 7.82 (1H,d,J=16.0 Hz), 7.99(2H,d,J=9.0 Hz), 8.10(1H,d,J=8.0 Hz), 8.45(1H,s), 10.27(1H,s), 12.81(1H,s).

EXAMPLE 63

Synthesis of 2-[(E)-3-oxo-3-(2-hydroxy-5-(4-(4-phenylbutoxy)benzamido)phenyl)-1-propenyl]imidazole {in the formula (1), $R^1$=H, $R^2$=2-OH, $R^3$=5-NHCOPh-4-O(CH$_2$)$_4$Ph, $R^4$=H}:

5'-Amino-2'-hydroxyacetophenone (1.51 g, 10 mmol) was dissolved in ethanol (50 ml), and di-t-butyl dicarbonate [(t-BuOCO)$_2$O] (2.61 g, 12 mmol) was added to the solution. The mixture was stirred at room temperature for 4 hours.

The resultant reaction mixture was dried to solid under reduced pressure, and hexane (30 ml) was added to the residue. Crystals deposited were collected by filtration and dried to obtain 1.90 g (yield: 76%) of 5'-t-butoxycarbonylamino-2'-hydroxyacetophenone.

Melting point: 107 to 107.5° C.; $^1$H-NMR δ ppm (CDCl$_3$): 1.52(9H,s), 2.64(3H,s), 6.43(1H,s), 6.90(1H,d,J= 9.0 Hz), 7.25(1H,dd,J=9.0, 2.0 Hz), 7.97(1H,d,J=2.0 Hz), 12.03(1H,s).

2-[(E)-3-Oxo-3-(5-t-butoxycarbonylamino-2-hydroxyphenyl)-1-propenyl]-1-(2-trimethylsilyl) ethoxymethylimidazole (1.93 g; yield: 60%) was obtained in the same manner as in Example 1 except that 1-(2-trimethylsilyl)ethoxymethyl-2-imidazole carbaldehyde (1.58 g, 7.0 mmol) and 5'-t-butoxycarbonylamino-2'-hydroxyacetophenone (1.76 g, 7.0 mmol) were used.

Melting point: 94 to 95° C.; $^1$H-NMR δ ppm (CDCl$_3$): −0.02(9H,s), 0.93(2H,t,J=8.0 Hz), 1.52(9H,s), 3.54(2H,t,J=8.0 Hz), 5.44(2H,s), 6.49(1H,s), 6.97(1H,d,J=9.0 Hz), 7.18 (1H,d,J=1.0 Hz), 7.25(1H,d,J=1.0 Hz), 7.55(1H,dd,J=9.0, 2.0 Hz), 7.80(1H,t,J=15.0 Hz), 7.92(1H,d,J=2.0 Hz), 8.07 (1H,d,J=15.0 Hz), 12.50(1H,s).

2-[(E)-3-Oxo-3-(5-t-butoxycarbonylamino-2-hydroxyphenyl)-1-propenyl]-1-(2-trimethylsilyl) ethoxymethylimidazole (1.84 g; 4.0 mmol) was dissolved in dichloromethane (4 ml), and trifluoroacetic acid (2 ml) was added to the solution under stirring at 0° C. Stirring was conducted further for 2 hours. The resultant reaction mixture was dried to solid under reduced pressure, and a saturated aqueous solution (10 ml) of sodium hydrogencarbonate was added to the residue to conduct extraction with chloroform. An organic layer was dried and then concentrated under reduced pressure. The resultant residue was subjected to column chromatography on silica gel to obtain 0.99 g (yield: 69%) of 2-[(E)-3-oxo-3-(5-amino-2-hydroxyphenyl)-1-propenyl]-1-(2-trimethylsilyl)ethoxymethylimidazole from a fraction eluted with 1% (v/v methanol-chloroform.

Melting point: 110 to 113° C.; $^1$H-NMR δ ppm (CDCl$_3$): 0.04(9H,s), 0.98(2H,t,J=8.0 Hz), 3.20–3.80(4H,m), 5.50 (2H,s), 6.80–7.40(5H,m), 7.85(1H,d,J=15.0 Hz), 8.15(1H,d,J=15.0 Hz), 12.28(1H,s).

2-[(E)-3-Oxo-3-(2-hydroxy-5-(4-(4-phenylbutoxy) benzamido)phenyl)-1-propenyl]-1-(2-trimethylsilyl) ethoxymethylimidazole (0.67 g; yield: 55%) was obtained in the same manner as in Example 62 except that 2-[(E)-3-oxo-3-(5-amino-2-hydroxyphenyl)-1-propenyl]-1-(2-trimethylsilyl)ethoxymethylimidazole (0.72 g, 2.0 mmol) and 4-(4-phenylbutoxy)benzoyl chloride (0.63 g, 2.2 mmol) were used.

Melting point: 135 to 136° C.; $^1$H-NMR δ ppm (CDCl$_3$): −0.03(9H,s), 0.92(2H,t,J=8.0 Hz), 1.78–1.90(4H,m), 2.71 (2H,t,J=7.0 Hz), 3.54(2H,t,J=8.0 Hz), 4.03(2H,t,J=7.0 Hz), 5.44(2H,s), 6.93(2H,d,J=9.0 Hz), 6.99(1H,d,J=9.0 Hz), 7.17–7.33(7H,m), 7.79(1H,d,J=15.0 Hz), 7.87(2H,d,J=9.0 Hz), 7.93(1H,dd,J=9.0,2.0 Hz), 8.02–8.07(2H,m), 8.26(1H,s), 12.53(1H,s).

The title compound (0.17 g; yield: 35%) was obtained in the same manner as in Example 61 except that 2-[(E)-3-oxo-3-(2-hydroxy-5-(4-(4-phenylbutoxy)benzamido) phenyl)-1-propenyl]-1-(2-trimethylsilyl) ethoxymethylimidazole (0.61 g, 1.0 mmol) and a 1 M solution (6 ml) of (n-Bu)$_4$NF in THF were used.

Melting point: 186 to 188° C.; $^1$H-NMR δ ppm (DMSO-d$_6$): 1.70–1.77(4H,m), 2.66(2H,t,J=7.0 Hz), 4.09(2H,t,J=7.0 Hz), 7.00(1H,d,J=9.0 Hz), 7.04(2H,d,J=9.0 Hz), 7.15–7.40 (7H,m), 7.60(1H,d,J=15.0 Hz), 7.87(1H,d,J=15.0 Hz), 7.91 (1H,dd,J=9.0,2.0 Hz), 7.96(2H,d,J=9.0 Hz), 8.35(1H,d,J=2.0 Hz), 10.07(1H,s), 11.96(1H,br), 12.80(1H,br).

PREPARATION EXAMPLE 1

The following compound was obtained in the same manner as in Example 1 except that 2-imidazole carbaldehyde (2) and acetophenone were used.

2-[(E)-3-Oxo-3-phenyl-1-propenyl]imidazole {in the formula (1'), $R^1=R^2=R^3=R^4=H$}

Melting point: 190.5 to 191.5° C.; $^1$H-NMR δ ppm (DMSO-d$_6$): 7.30(2H,s), 7.51(1H,d,J=15.0 Hz), 7.60–7.63 (2H,m), 7.65–7.70(1H,m), 7.85(1H,d,J=15.0 Hz), 8.00–8.07 (2H,m), 12.80(1H,s).

TEST EXAMPLE 1

Test of IL-4-production Suppression

A human T cell strain, ATL-16T(−) was poured into each well of a 48-well microplate at a concentration of 1×10$^6$ cells/0.5 ml/well (n=3), and a stimulator (PMA, 20 nM) and a compound to be tested were added at the same time to incubate the microplate at 37° C. for 48 hours in the presence of 5% CO$_2$. After the incubation, supernatant solutions (100 µl) were collected to determine an amount of IL-4 produced by means of a human IL-4 EIA kit (product of R & D SYSTEMS CO.). The suppression rate of IL-4 production was calculated out in accordance with the following equation:

Suppression rate (%)=[(Amount of IL-4 produced when the stimulator was added)−(Amount of IL-4 produced when the stimulator and test agent were added)]/[(Amount of IL-4 produced when the stimulator was added)−(Amount of IL-4 produced when no stimulator was added)]×100

The results are shown in Table 1.

TABLE 1

| Compound | Suppression rate of IL-4 production (%) | | | |
| --- | --- | --- | --- | --- |
| No. | $10^{-9}$ M | $10^{-8}$ M | $10^{-7}$ M | $10^{-6}$ M |
| Example 1 | 39.7 | 49.0 | 56.5 | 71.0 |
| Example 2 | 43.4 | 49.1 | 56.6 | 81.9 |
| Example 4 | 46.2 | 50.3 | 59.2 | 73.3 |
| Example 5 | 43.8 | 58.7 | 71.4 | 70.7 |
| Example 7 | 50.6 | 49.0 | 60.9 | 87.5 |
| Example 8 | 44.5 | 50.9 | 58.4 | 94.3 |
| Example 10 | 42.1 | 51.1 | 57.1 | 72.8 |
| Example 11 | 60.0 | 65.1 | 72.7 | 93.5 |
| Example 12 | 53.2 | 58.4 | 68.1 | 82.2 |
| Prep. Ex. 1 | 57.6 | 71.5 | 81.9 | 95.2 |

TEST EXAMPLE 2

Test of IL-4-production Suppression

A human T cell strain, ATL-16T(−) was poured into each well of a 96-well microplate at a concentration of 5×10$^5$ cells/0.2 ml/well (n=3), and a stimulator (PMA, 20 nM) and a compound to be tested were added at the same time to incubate the microplate at 37° C. for 48 hours in the presence of 5% CO$_2$. After the incubation, supernatant solutions were collected to determine an amount of IL-4 produced by means of an EIA kit (product of BIO SOURCE CO.). Thereafter, the IC$_{50}$ of each test compound was calculated in accordance with the probit method. The results are shown in Table 2.

TABLE 2

| Compound | Suppression of IL-4 production, IC$_{50}$ (nM) |
| --- | --- |
| Example 34 | 2.39 |
| Example 44 | 6.73 |
| Example 46 | 0.94 |
| Example 47 | 8.06 |
| Example 48 | 1.80 |
| Example 49 | 2.67 |
| Example 50 | 1.94 |
| Example 53 | 1.97 |
| Example 54 | 0.26 |
| Example 55 | 1.64 |
| Example 57 | 7.95 |

TABLE 2-continued

| Compound | Suppression of IL-4 production, $IC_{50}$ (nM) |
|---|---|
| Example 58 | 3.76 |
| Example 59 | 1.39 |
| Example 62 | 0.46 |
| Example 63 | 3.11 |

FORMULATION EXAMPLE 1

Tablet Preparation

| | |
|---|---|
| Compound of Example 54 | 10 mg |
| Crystalline cellulose | 60 mg |
| Lactose | 60 mg |
| Hydroxypropyl cellulose | 18 mg |
| Magnesium stearate | 2 mg |
| Total | 150 mg |

A tablet preparation having the above composition was formulated in accordance with a method known per se the art. The tablet preparation may be formed into a sugar-coated or film-coated tablet preparation as needed.

FORMULATION EXAMPLE 2

Capsule Preparation

| | |
|---|---|
| Compound of Example 54 | 10 mg |
| Precipitated silicic anhydride | 25 mg |
| Lactose | 90 mg |
| Starch | 50 mg |
| Talc | 25 mg |
| Total | 200 mg |

The above components were filled into No. 1 Capsules to obtain a capsule preparation.

FORMULATION EXAMPLE 3

Granule Preparation

| | |
|---|---|
| Compound of Example 54 | 10 mg |
| Lactose | 640 mg |
| Corn starch | 200 mg |
| Sodium carboxymethyl cellulose | 20 mg |
| Hydroxypropyl cellulose | 130 mg |
| Total | 1000 mg |

A granule preparation having the above composition was formulated in accordance with a method known per se in the art.

FORMULATION EXAMPLE 4

Powder Preparation

| | |
|---|---|
| Compound of Example 54 | 10 mg |
| Precipitated silicic anhydride | 20 mg |
| Precipitated calcium carbonate | 10 mg |
| Lactose | 290 mg |
| Starch | 70 mg |
| Total | 400 mg |

A powder preparation having the above composition was formulated in accordance with a method known per se in the art.

FORMULATION EXAMPLE 5

Injection Preparation

| | |
|---|---|
| Compound of Example 5 | 1 mg |
| Hardened castor oil | 85 mg |
| Propylene glycol | 60 mg |
| Glucose | 50 mg |
| Total | To 1 ml with distilled water for injection |

An injection preparation having the above composition was formulated in accordance with a method known per se in the art.

FORMULATION EXAMPLE 6

Drip Infusion Preparation

| | |
|---|---|
| Compound of Example 5 | 5 mg |
| Glucose | 5000 mg |
| Disodium hydrogenphosphate | 10 mg |
| Citric acid | 14.5 mg |
| Total | To 100 ml with distilled water for injection |

A drip infusion preparation having the above composition was formulated in accordance with a method known per se in the art.

FORMULATION EXAMPLE 7

Cream Preparation

| | |
|---|---|
| Compound of Example 48 | 50 mg |
| White petrolatum | 5 g |
| Medium chain fatty acid triglyceride | 15 g |
| Glycerol monostearate | 3.4 g |
| Polyoxyethylene cetyl ether (25 E.O.) | 1.6 g |
| Methyl p-hydroxybenzoate | 0.2 g |
| Butyl p-hydroxybenzoate | 0.1 g |
| Sodium edetate | 0.02 g |
| Total | To 100 g with purified water |

The above components were used in the above respective amounts to formulate a cream preparation in accordance with a method known per se in the art.

FORMULATION EXAMPLE 8

Ointment Preparation

| | |
|---|---|
| Compound of Example 48 | 50 mg |
| Diethyl sebacate | 5 g |
| Sorbitan sesquioleate | 3 g |
| Purified water | 3 g |

-continued

| Sodium edetate | 0.02 g |
| Total | To 100 g with white petrolatum |

The above components were used in the above respective amounts to formulate an ointment preparation in accordance with a method known per se in the art.

Japanese Patent Application No. 9-346215, filed on Dec. 16, 1997, is incorporated herein by reference in its entirety.

What is claimed is:

1. An imidazole compound represented by the following general formula (1'):

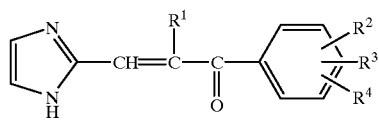
(1')

wherein $R^1$ is a hydrogen atom, or an alkyl, alkoxy or alkoxycarbonyl group, and $R^2$, $R^3$ and $R^4$ are the same or different from one another and are independently a hydrogen or halogen atom, or an alkyl group, a halogenoalkyl group, a hydroxyl group, an alkoxy group, a carboxyl group, a nitro group, a tetrahydropyranyloxy group, an alkoxyalkoxy group, an alkoxycarbonyl group, a cyano group, a tetrazolyl group, a phenyl group which may be substituted, a phenoxy group which may be substituted, a benzyloxy group which may be substituted, an amino group which may be substituted, or a dioxolanyl group which may be substituted, or $R^3$ and $R^4$ may form a fused aromatic ring, which may be substituted, together with a benzene ring on which $R^3$ and $R^4$ are substituted, with the proviso that $R^1$, $R^2$, $R^3$ and $R^4$ are not hydrogen atoms at the same time, or a salt thereof.

2. A pharmaceutical composition comprising, as an active ingredient, an imidazole compound represented by the following general formula (1):

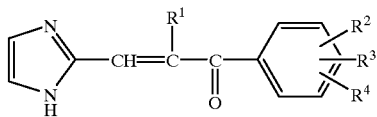
(1)

wherein $R^1$ is a hydrogen atom, or an alkyl, alkoxy or alkoxycarbonyl group, and $R^2$, $R^3$ and $R^4$ are the same or different from one another and are independently a hydrogen or halogen atom, or an alkyl group, a halogenoalkyl group, a hydroxyl group, an alkoxy group, a carboxyl group, a nitro group, a tetrahydropyranyloxy group, an alkoxyalkoxy group, an alkoxycarbonyl group, a cyano group, a tetrazolyl group, a phenyl group which may be substituted, a phenoxy group which may be substituted, a benzyloxy group which may be substituted, an amino group which may be substituted, or a dioxolanyl group which may be substituted, or $R^3$ and $R^4$ may form a fused aromatic ring, which may be substituted, together with a benzene ring on which $R^3$ and $R^4$ are substituted, or a salt thereof, and a pharmaceutically acceptable carrier.

3. The pharmaceutical composition according to claim 2, which is a cytokine-production suppressor.

4. The pharmaceutical composition according to claim 2, which is an immune function modulator.

5. A pharmaceutical composition comprising the imidazole compound or the salt thereof according to claim 2 and pharmaceutically acceptable carrier.

6. A method of treating a disease based on the production of cytokine, or a disease caused by immune function disorder, which comprises administering an effective amount of the imidazole compound or the salt thereof according to claim 2.

7. The method according to claim 6, wherein the disease caused by immune function disorder is a collagen disease, systemic lapus erythematosus or allergic disease.

* * * * *